United States Patent [19]

Nyström et al.

[11] Patent Number: 5,525,736

[45] Date of Patent: Jun. 11, 1996

[54] PROCESS FOR THE PRODUCTION OF CYCLIC SULFONIUM SALTS

[75] Inventors: Jan-Erik Nyström, Kista; Per Engelhardt, Stockholm; Katarina Beierlein, Uppsala; Mikael Sellén, Göteborg; Björn Elman, Märsta; Jan Vågberg, Sollentuna; Martin Nylöf, Södertälje, all of Sweden

[73] Assignee: Ciba-Geigy Corporation, Tarrytown, N.Y.

[21] Appl. No.: 393,519

[22] Filed: Feb. 23, 1995

Related U.S. Application Data

[63] Continuation of Ser. No. 84,192, filed as PCT/SE91/00749, Nov. 6, 1991 published as WO93/09112 May 13, 1993, abandoned.

[51] Int. Cl.$^6$ .............. C07D 333/06; C07D 335/02; C07D 337/04; C07D 337/06
[52] U.S. Cl. .............. 549/5; 549/3; 549/6; 549/9; 549/13; 549/59; 549/12; 549/15; 549/49; 549/29
[58] Field of Search .............. 549/59, 9, 23, 549/13, 29, 49, 78, 5, 3

[56] References Cited

U.S. PATENT DOCUMENTS

| | | | |
|---|---|---|---|
| 3,660,431 | 5/1972 | Hatch et al. | 549/41 |
| 3,898,247 | 8/1975 | Schmidt et al. | 549/59 |
| 3,903,056 | 9/1975 | Schmidt et al. | 549/59 |
| 3,915,991 | 10/1975 | Schmidt et al. | 549/29 |
| 4,058,400 | 11/1977 | Crivello | 96/86 P |
| 4,058,401 | 11/1977 | Crivello | 96/115 R |
| 4,089,877 | 5/1978 | Klinger et al. | 549/59 |
| 4,118,297 | 10/1978 | Broxterman et al. | 549/29 |
| 4,130,543 | 12/1978 | Doorakian et al. | 528/125 |
| 4,196,298 | 4/1980 | Klinger et al. | 549/76 |
| 4,282,373 | 8/1981 | Guest et al. | 549/79 |
| 4,477,640 | 10/1984 | Schmidt et al. | 549/78 |
| 4,528,384 | 7/1985 | Schmidt et al. | 549/78 |
| 4,883,740 | 11/1989 | Schwalm et al. | 430/270 |
| 4,885,355 | 12/1989 | Wessling et al. | 549/62 |
| 4,929,556 | 5/1990 | Cheng et al. | 435/180 |
| 5,013,814 | 5/1991 | Roth et al. | 528/90 |
| 5,101,053 | 3/1992 | Boettcher | 556/64 |
| 5,191,124 | 3/1993 | Schwalm et al. | 568/18 |
| 5,223,591 | 6/1993 | Nyander et al. | 549/41 |
| 5,238,747 | 8/1993 | Schmidt et al. | 428/421 |

FOREIGN PATENT DOCUMENTS

| | | |
|---|---|---|
| 2050196 | 4/1971 | Germany. |
| 1481424 | 7/1977 | United Kingdom. |
| WO/90/11303 | 10/1990 | WIPO. |

OTHER PUBLICATIONS

March, Advanced Organic Chemistry, Third Edition (1985).
Gronowitz Salo, Thiophene and its Derivatives, Part One, (1985) p. 1.
Chem. Ber. 1936, 69, 492–499.
Helvetica Chimica Acta, vol. 53, Fasc. 6 (1970), Nr. 146–147, 1271–1285.
J. Org. Chem. 1963, Nr. 28, 235–236.
Tetrahedron Letters No. 13, 1101–1104, (1979).
Heterocycles, vol. 26, No. 9, 1987.
J. Org. Chemistry, vol. 24, 1428, (1959).
Makromol. Chem., 1985, 136.
Chemical Abstracts, vol. III, 1989, 40092y (JP63/221111).
Journal of Polymer Science. Polymer Letters Edition, vol. 23, 359–363 (1985).
Journal of Coatings Technology, vol. 53, No. 675 Apr. 1981 pp. 43–51.
Houben–Weyl, 1955, IX, 171–194.
Houben–Weyl Bd. E 11, 1985, 405–454.
The Chemistry of Sulphonium Group Edited by Sterling and Patai, 1981, Chapter 11.
The Chemistry of the Sulphonium Group Edited by Sterling and Patai, 1981, Chapter 13.
Chem. Ber. 1910, 43, 3422–3429.
Chem. Ber. 1929, A, 62, 127–131.
J. Am. Chem. Soc. vol. 24, pp. 1428–1432 (1959).

*Primary Examiner*—Allen J. Robinson
*Assistant Examiner*—Deborah Lambkin
*Attorney, Agent, or Firm*—William A. Teoli; Michele A. Kovaleski

[57] ABSTRACT

A process for the production of a 5–7 membered ring cyclic sulfonium salt compound, including a 5–7 membered ring cyclic sulfonium salt compound having a non-nucleophilic anion, is described. Members of the latter group are potentially useful as initiators for cationic polymerizations. The process comprises reacting a 1.4-, 1.5-, or 1.6-diol compound or a 5–7 membered ring cyclic ether compound with a mercapto compound and a strong protonic acid yielding the cyclic sulfonium salt compound. Some compounds described are also novel compounds per se.

23 Claims, 1 Drawing Sheet

PROCESS FOR THE PRODUCTION OF CYCLIC SULFONIUM SALTS

This application is a continuation of application Ser. No. 08/084,192, filed Jul. 2, 1993, abandoned and which is a 371 of PCT/SE91/00749 Nov. 6, 1991, published as WO93/09112 May 13, 1993.

The present invention relates to a process for the production of a 5–7 membered ring cyclic sulfonium salt compound, including a 5–7 membered ring cyclic sulfonium salt compound having a non-nucleophilic anion. Representatives of the latter group are potentially useful as initiators for cationic polymerizations. More specifically, the invention relates to a process comprising reacting a 1,4-, 1.5-, or 1,6-diol compound or a 5–7 membered ring cyclic ether compound with a mercapto compound and a strong protonic acid yielding the cyclic sulfonium salt compound.

The process of the invention is general, efficient, and performable in one step resulting in a product in high yield and purity, and a wide variety of 5–7 membered ring cyclic sulfonium salt compounds can be produced by the invention. The invention further relates to some compounds which are novel compounds per se. These novel compounds were produced by the process of the invention.

BACKGROUND OF THE INVENTION

Tris organo sulfonium salts is an important class of sulfur compounds. Sulfonium salts have received renewed interest since the discovery that some triaryl sulfonium salts could be utilized as latent initiators for cationic polymerization, as disclosed in U.S. Pat. Nos. 4,058,400 and 4,058,401. These salts were activated photochemically. More recently, it has been found that some benzylic sulfonium salts can be utilized as latent thermal initiators for cationic polymerization, see for example PCT-application SE 90/00179 (23 Mars 1989); U.S. Pat. No. 5,013,814 (16 Jan. 1989); Japan-patent no. JP 63,221,111 (11 Mars 1987) Chem. Abstr. 1989, 111, 40092; Endo. T and Uno, H. *J. Polym. Sci., Polym. Lett. Ed.* 1985, 23,359; Pappas S. P. and Hill. L. W. *J. Coat. Technol.* 1981, 53, 43.

The latter have been shown to be thermally labile and decompose upon heating, leading to heterolytic cleavage of a sulfur-carbon bond yielding a sulfide and a carbocation capable of initiating the cationic polymerization. It has also been shown that the propagation rate of the cationic polymerization is very much dependent of the nature of the anion and as a result it is necessary that the sulfonium salt initiator has a non-nucleophilic anion $X^-$, e.g. $SbF_6^-$, $PF_6^-$, $AsF_6^-$, and $BF_4^-$, as disclosed in U.S. Pat. Nos. 4,058,400 and 4,058,401. *J. Appl. Polymer Sci.* 1978, 43, 4826 and *Makromol. Chem.* 1985. 136.

PRIOR ART

Methods for producing sulfonium salts have been extensively reviewed, see for example, Methoden der Organischen Chemie (Houben-Weyl) 1955, Volume IX, 171 ff, and 1985, supplement E 11,405 ff; Lowe, P. A. The Chemistry of the Sulphonium Group, Ed. Stirling and Patai 1981, 267–313. More specifically, synthetic routes for preparing cyclic sulfonium salts have also been described, see for example Dittmer, D. C. and Patwardhan, B. H. The Chemistry of the Sulphonium Group Ed. Stirling and Patai, 1981, 387–522. Some of the methods most frequently used include monoalkylation of a sulfide or dialkylation of a mercaptan with a powerful alkylating agent R–Y, such as an alkyl halide, whereby the leaving group of the alkyl halide becomes the counter ion of the sulfonium cation. However, these methods are suffer from a number of disadvantages;

Firstly, there are limitations in alkylating agents which are reactive enough to succeed in alkylating a sulfide. Therefore, in the most cases, the structural scope of R is limited to methyl, primary alkyl, or benzylic groups. Among the alkyl halides, alkyl iodides are normally required and only in favorable cases bromides can be used.

Secondly, due to the limited access of alkylating agent consisting of any of the anions above as the nucleofuge. Meerwein's salt (triethyl oxonium tetrafluoroborate; $Et_3O^+ BF_4^-$) is an exception, an ion-exchanging step is required in order to prepare a cyclic or acyclic sulfonium salt having a non-nucleophilic anion, leading to additional process steps. The ion-exchange is achieved by addition of a salt $A^+X^-$ (A is usually an alkali metal or silver) and from the mixture the desired cyclic or acyclic sulfonium salt has to be isolated. The efficiency of such a metathesis step relies on complete and selective extraction of the desired $R_3S^+X^-$ to a suitable organic solvent or finding a solvent system wherein $R_3S^+Y^-$ is soluble and $R_3S^+X^-$ precipitates. The conditions of a complete metathesis would more or less depend on the substrate since structural changes very often affects solubility properties and the conditions have to be optimized in each case. The use of a silver salt as a precipitating agent for removal of the halide is another drawback for economical reasons, see equation 1.

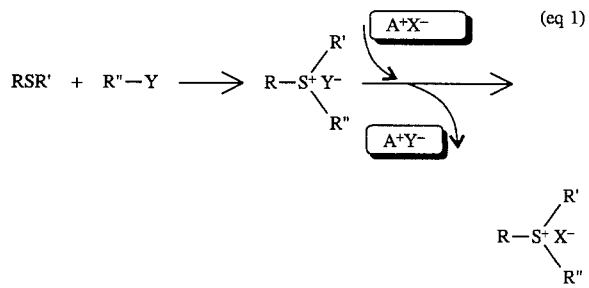

A much more attractive method for making a sulfonium salt having a non-nuclephilic anion is the acid-promoted alkylation of sulfur with alcohols or ethers whereby the anion of the strong acid becomes the counter-ion of the sulfonium ion. Methods for producing sulfonium salts having non-nucleophilic anions by alkylation of sulfides with alcohols or ethers promoted by protonic acids are previously known, such as those described in: Fichter, Sjöstedt Chem. Ber. 1910, 43, 3422; Hinsberg Chem. Ber. 1929, 62, 127 and 1936, 69, 492; Milligan, Minor J. Org. Chem. 1963, 28, 235; Bosshard Helv. Chim. Acta 1970, 53, 1271; Julia Tetrahedron Lett. 1979, 1101; Okuma et al, Heterocycles 1987,26, 2343; PCT-application SE 90/00179 (23 Mars 1989); U.S. Pat. No. 5,013,814 (16 Jan. 1989).

However, a general, convenient, and efficient method has not yet been developed starting from simple mercaptans. Syntheses of some cyclic sulfonium salts made by an intra-molecular alkylation of a mercaptan promoted by acid have been reported—Eastman. R. H. and Kritchevsky, G. J. Org. Chem. 1959, 24, 1428. However, in these examples, very complicated mercaptans were used, which had to be synthesized prior to the cyclization. These examples lack generality.

PCT-application SE 90/00179 describes some cyclic sulfonium salts having non-nucleophilic anions used as latent thermal initiators for cationically polymerizable compounds. It was shown that the thermal stability of 2-aryl tetrahydrothiophenium sulfonium salts could be controlled by the the aryl group. All salts were synthesized by known methods utilizing strong electrophiles such as alkyl halides and Meerwein's salt for alkylation of cyclic sulfides. These methods suffer from the drawbacks mentioned above. Such salts can now be produced much more efficiently and in higher yields and purity using the process of the present invention. In addition, the present invention allows the synthesis of a wide variety of different 2-aryl tetrahydrothiophenium sulfonium salts allowing fine tuning of the initiator properties such as initiating temperature, solubility and "shelf life".

SUMMARY OF THE INVENTION

The present invention provides a novel and efficient process for the production of a 5–7 membered ring cyclic sulfonium salt compound, including a 5–7 membered ring cyclic sulfonium salt compound having a non-nucleophilic anion. Members of the latter group are potentially useful as initiators for cationic polymerizations. More specifically, the process comprises reacting a 1,4-, 1,5-, or 1,6-diol compound or a 5–7 membered ring cyclic ether compound with a mercapto compound and a strong protonic acid yielding the cyclic sulfonium salt compound having the desired anion.

The invention also provides a general process for the production of a wide variety of structurally different cyclic sulfonium salt compounds. The structural plurality available by this invention includes the sulfur-containing heterocyclic ring, which is derived from the diol or the cyclic ether reactant, the "R"-substituent which is derived from the mercaptan reactant, and $X^-$ which is derived from the acid reactant. These three reactants can be varied independently allowing production of a large number of possible 5–7 membered ring cyclic sulfonium salts. In addition, by using either a di- or polyfunctional mercapto compound or a di- or polyfunctional diol or cyclic ether compound as the reactant it is possible to produce a di- or polyfunctional sulfonium salt, i.e. a compound containing two or more cyclic sulfonium groups.

The invention provides mild reaction conditions and room temperature or slightly above is generally applicable. The process is very efficient and substantially equimolar amounts (relative to the functional groups) of the diol/cyclic ether compound and the mercapto compound with a slight excess of the protonic acid is sufficient to form the sulfonium salt compound quantitively. Since the sulfonium salt compound is formed quantitatively (in most cases) the workup simply includes removal of excess protonic acid reactant followed by recrystallization of the crude product, thus making the process very easily adaptable for large scale production.

It is well known to those skilled in the art that many diols and cyclic ethers are generally easily accessible, both as commercially available starting materials and also by the numerous organic transformations available for the production of diols and ethers. The invention allows synthesis of a wide variety of 5 to 7 membered cyclic sulfonium salts by simply varying the diol or ether reactant.

The mercapto compound, according to this invention, can be selected from a wide variety of structurally different mercaptans such as methyl mercaptan, primary, secondary, tertiary alkyl mercaptans, aryl mercaptans, dimercaptans, and polymercapto compounds, consisting of both straight, cyclic and branched chain hydrocarbyl groups.

According to this invention, any strong protonic acid can furnish the transformation of the diol/cyclic ether compound and the mercapto compound to the sulfonium salt compound. This implies that by selecting the protonic acid, structurally different sulfonium salt compounds having a wide variety of anions, i.e. anions of desired properties, can be produced, including sulfonium salt compounds having non-nucleophilic anions.

The possibilities of producing pure and structurally different cyclic sulfonium salts having different anions are thereby markedly improved since the process does not introduce any other anions, than the corresponding base to the strong acid, that otherwise could contaminate the desired sulfonium salt.

The structural scope of the alkylating agent according to the prior art, i.e. where a cyclic sulfide is alkylated intermolecularly, is in practice limited to methyl and primary alkyl halides. Synthesis of cyclic sulfonium salts having a secondary or tertiary hydrocarbyl group attached to the sulfur atom by alkylation of a sulfide with a secondary or a tertiary alkyl halide are not possible. There are no such limitations in the present invention, wherein the diol or the cyclic ether group, promoted by the strong protonic acid, alkylates the mercapto group. The cyclic sulfonium salts having the structures discussed above can easily be produced in high yields and purity. As noted above, the mercaptan can be selected from methyl mercaptan, primary, secondary, or tertiary alkyl, or aryl mercaptans.

According to the process of the invention, either a diol or the corresponding cyclic ether can be used as one of the reactants. The diol or the corresponding cyclic ether can be mono-, di- or polyfunctional. At an early stage of the reaction under the conditions of the invention, i.e. the presence of a strong protonic acid, the diol is first transformed to the corresponding cyclic ether, see FIG. 1. Such transformations are well known from the literature, see for example Schmoyer et al, Nature 1960, 187, 592, where 1,4-butanediol was transformed to tetrahydrofuran. However, under the specific conditions of the present invention, i.e. in the presence of a mercaptan and a strong protonic acid, the reaction proceeds directly to the sulfonium salt product via the intermediate cyclic ether product and an intermediate sulfidoalcohol. Consequently, there is an equivalence between a diol and the corresponding cyclic ether and either of them could be used as one of the reactants, see equation 2.

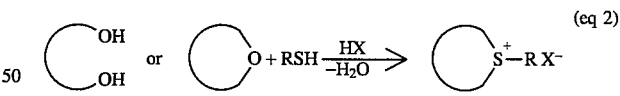

(eq 2)

The invention very efficiently utilizes the reactants since the wasted leaving group is one or two water molecule/s (18 or 36 grams per mole of formed sulfonium salt) when using a cyclic ether or a diol as the alkylating agent, as compared to the prior art where in the first step iodide (129 grams per mol of sulfonium salt) is wasted when utilizing an alkyl iodide as the alkylating agent. In order to obtain the desired non-nucleophilic anion, the necessary ion-exchange leads to an additional waste, usually an alkali metal such as sodium or potassium, or silver; 23, 39, and 108 atomic units, respectively. In summary, the two-step procedure: an alkyl iodide followed by sodium hexafluorophosphate would produce a waste of 152 g of sodium iodide, whereas the one-step diol route produces 32 g of waste per mole of sulfonium salt which in the latter case is water. Consequently, more of the reactants ends up in the sulfonium salt by employing the present invention.

Other objectives and advantages will become apparent from the detailed description of the invention which follows.

DETAILED DESCRIPTION OF THE INVENTION

The present invention relates to a process for the production of a 5–7 membered ring cyclic sulfonium salt compound comprising reacting a 1,4-, 1,5-, or 1,6-diol compound or a 5–7 membered ring cyclic ether compound with a mercapto compound and a strong protonic acid.

The reaction is performed by adding the strong protonic acid to the mercapto compound and the resulting mixture is added to the diol or cyclic ether compound, or the strong protonic acid is added to a mixture containing the mercapto compound and the diol or cyclic ether compound, in substantially equimolar amounts with respect to the functional groups involved.

The reaction is thus performed in the above preferred order of mixing of the reactants. Reverse order of mixing, i.e. first mixing the strong protonic acid with the diol/cyclic ether compound in the absence of the mercapto compound, usually results in unwanted and rapid polymerization of the diol/cyclic ether compound.

According to this invention the mercapto compound can be mono-, di-, or polyfunctional, with respect to the mercapto group. The diol or cyclic ether compound can be mono-, di-, or polyfunctional, with respect to the diol or cyclic ether group. Polyfunctionality relates to three or more groups, preferably 3–50 groups for the diol or cyclic ether compound and preferably 3–500 groups for the mercapto compound.

The present invention also relates to the process above for the production of a cyclic sulfonium salt compound having a non-nucleophilic anion. Typically, a non-nucleophilic anion is characterized by a polyatomic molecule, $MZ_n^-$ consisting of a central atom M symmetrically surrounded by 4 or 6 atoms Z which are more electronegative than the central atom. A non-nucleophilic anion have none or very little ability to form covalent bonds and usually they are the corresponding base to a very strong protonic acid.

According to one embodiment of the invention the process comprises reacting: (a) a mercapto compound having the formula $R^1$—SH, wherein $R^1$ in a monofunctional mercaptan represents methyl, primary, secondary, or tertiary alkyl or cycloalkyl; aryl, preferably phenyl, which is unsubstituted or mono- or independently polysubstituted by alkyl, cycloalkyl, alkoxy, thioalkoxy, phenyl, phenoxy or thiophenoxy; and naphthyl; arylalkyl, preferably benzyl, which is unsubstituted or mono- or independently polysubstituted by alkyl, alkoxy or thioalkoxy; or $R^1$ in a di- or a polyfunctional mercaptan represents —[A-SH]$_m$, wherein $m \geq 1$, and A independently represents alkylene, preferably $C_2$–$C_{20}$, arylene, preferably phenylene, biphenylene or naphthylene; alkylenebisaryl preferably methylenebiphenyl; or aralkylene, preferably xylylene, with (b) a diol compound selected from the group consisting of formula I:

I = 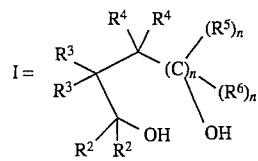

wherein
n is 1, 2, or 3,
$R^2$ independently represents hydrogen, alkyl, cycloalkyl, or aryl, preferably

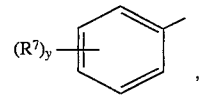

wherein y is an integer between 0 and 5, and $R^7$ independently represents alkyl, alkoxy, thioalkoxy, halogen, cyano, alkyl sulfonyl, aryl sulfonyl, preferably phenyl sulfonyl, aryl, aryloxy, or thioaryloxy, wherein the aryl group preferably is phenyl which is unsubstituted or mono- or independently polysubstituted by alkyl, cycloalkyl, alkoxy, thioalkoxy, halogen, phenoxy, thiophenoxy, cyano, alkyl sulfonyl, or aryl sulfonyl, preferably phenyl sulfonyl, $R^3$ independently represents hydrogen, alkyl, cycloalkyl, aryl, preferably phenyl, which is unsubstituted or mono- or independently polysubstituted by alkyl, cycloalkyl, alkoxy, thioalkoxy, halogen, phenoxy or thiophenoxy, $R^4$ independently represents hydrogen, alkyl, cycloalkyl, aryl, preferably phenyl, which is unsubstituted or mono- or independently polysubstituted by alkyl, cycloalkyl, alkoxy, thioalkoxy, halogen, phenoxy or thiophenoxy, or $R^3$ and $R^4$ together form an aryl group fused with the corresponding carbon atoms of the carbon-carbon backbone chain, preferably

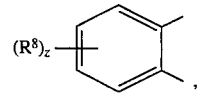

wherein z is an integer between 0 and 4, and $R^8$ independently represents alkyl, alkoxy, thioalkoxy, halogen or phenyl, $R^5$ independently represents hydrogen, alkyl, cycloalkyl, aryl, preferably phenyl, which is unsubstituted or mono- or independently polysubstituted by alkyl, cycloalkyl, alkoxy, thioalkoxy, halogen, phenoxy or thiophenoxy, $R^6$ independently represents hydrogen, alkyl, cycloalkyl, aryl, preferably phenyl, which is unsubstituted or mono- or independently polysubstituted by alkyl, cycloalkyl, alkoxy, thioalkoxy, halogen, phenoxy or thiophenoxy, or (c) a cyclic ether compound selected from the group consisting of formula II:

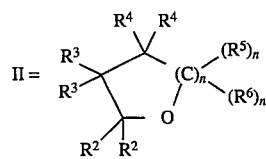

wherein n, $R^2$, $R^3$, $R^4$, $R^5$, and $R^6$ are as defined above, (d) and a strong protonic acid having the formula HX, wherein X represents a halogen or a group of the formula $MY_r$, wherein M represents Sb, P, B, As, or Cl; Y represents a halogen or oxygen; and r is an integer between 4 and 6, or X represents a group $RSO_3$ wherein R is OH alkyl, aryl or halogen substituted alkyl or aryl group, yielding a monofunctional cyclic sulfonium salt compound, when $R^1 \neq$—$[A\text{-}SH]_m$, having the following structural formula III-1:

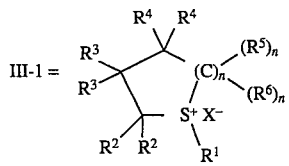

wherein n, $R^1$, $R^2$, $R^3$, $R^4$, $R^5$, $R^6$, and X are as defined above with the exception of that $R^1 \neq$—$[A\text{-}SH]_m$; or a di- or polyfunctional cyclic sulfonium salt compound, when $R^1=$—$[A\text{-}SH]_m$, having the following structural formula III-2:

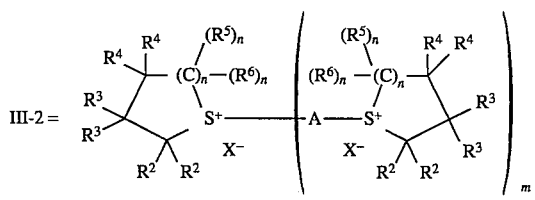

wherein n, m, A, $R^2$, $R^3$, $R^4$, $R^5$, $R^6$, and X are as defined above.

The reaction of the process involves displacement of the oxygen atom/s by the sulfur atom, yielding the cyclic sulfonium salt compound having the structural formulae above. The invention also comprises a rearrangement reaction, under the conditions of the process as defined above; When the diol compound of formula I) or the cyclic ether compound of II), when n=1 and $R^3$ and $R^4$ together form a fused aryl group as defined, one $R^2$ can additionally define an 1-alkenyl, $(R^9)_2C=C(R^{10})$—, wherein $R^9$ and $R^{10}$ independently represent hydrogen, alkyl, cycloalkyl, aryl, preferably phenyl, or a 5–7 membered ring formed by $R^9$ and $R^{10}$; preferably hydrogen, i.e. a vinyl group, yielding a cyclic sulfonium salt compound having the following structural formula IV:

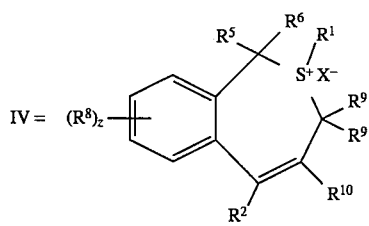

wherein $R^1$, $R^2$, $R^5$, $R^6$, $R^8$, and z are as defined, exept that $R^1 \neq$—$[A\text{-}SH]_m$.

Mercapto compounds which are useful in this reaction can be selected from mono-, di- or polyfunctional mercaptans. Suitable monofunctional mercaptans can be selected from methyl mercaptan, primary, secondary, or tertiary alkyl or cycloalkyl mercaptans, in which the term "alkyl" includes both straight and branched chain saturated hydrocarbyl moieties and generally includes moieties having from 2 to 20 C-atoms, including ethyl, n-propyl, iso-propyl, n-butyl, iso-butyl, sec-butyl, t-butyl, n-pentyl, iso-pentyl, sec-pentyl, neo-pentyl, n-hexyl, iso-hexyl, n-heptyl, iso-heptyl, octyl, nonyl, decyl, undecyl, dodecyl, hexadecyl, and octadecyl moieties, preferably the moieties having 1 to 12 C-atoms, and the term "cycloalkyl" includes cyclic saturated hydrocarbyl moieties and generally includes moieties having from 3 to 7 C-atoms in the cyclic moiety, preferably 5 to 7, such as cyclopentyl, cyclohexyl, and cycloheptyl in which the cyclic moiety can be directly bonded to the mercapto group or separated from the mercapto group by an alkylene group, such as methylene. Further monofunctional mercaptans which are useful in this reaction can be selected from aryl mercaptans, preferably phenyl mercaptans, which are unsubstituted or mono- or independently polysubstituted by alkyl, preferably $C_1$–$C_8$, cycloalkyl, preferably $C_5$–$C_7$, alkoxy, preferably $C_1$–$C_8$, thioalkoxy, phenyl, phenoxy, or thiophenoxy, or naphtyl mercaptan; arylalkyl mercaptans, preferably benzyl mercaptans, which are unsubstituted or mono- or independently polysubstituted by alkyl, alkoxy, or thioalkoxy. Preferred monofunctional mercaptans in the reaction are primary, secondary, and tertiary alkyl, aryl, and benzyl mercaptans, most preferably the primary, secondary, and tertiary $C_2$–$C_{12}$ alkyl mercaptans.

Suitable di- and polyfunctional mercaptans in this reaction can be selected from compounds of the general formula HS—$[A\text{-}SH]_m$, wherein $m \geq 1$, and A independently represents alkylene which can be substituted, preferably $C_2$–$C_{20}$, for example ethylene, propylene, butylene, pentylene, hexylene; arylene, preferably phenylene, biphenylene or naphthylene; alkylenebisaryl, preferably metylenebifenyl; or aralkylene, preferably xylylene. Examples of dimercaptans are: 1,2-ethane-dithiol, 1,3-propane-dithiol, 1,4-butane-dithiol, 2,3-butane-dithiol, 1,6-hexane-dithiol, and $\alpha,\alpha'$-dimercapto-p-xylene. Polymercaptans can consist of an oligomeric or polymeric chain having pendant mercapto groups.

Diol or cyclic ether compounds which are useful in this reaction can be selected from mono-, di- or polyfunctional diols or cyclic ethers. Suitable monofunctional diols and cyclic ethers can be selected from 1,4-, 1,5-, 1,6-diols, or 5–7 membered ring cyclic ether compounds (i.e. tetrahydrofurans, tetrahydropyrans, or hexahydrooxepins) respectively, which are i) unsubstituted, or ii) mono- or independently polysubstituted by alkyl, preferably $C_1$–$C_8$, cycloalkyl, preferably $C_5$–$C_7$, 1-alkenyl, preferably vinyl, aryl preferably phenyl, which is unsubstituted or mono- or independently polysubstituted by alkyl, preferably $C_1$–$C_{12}$, cycloalkyl, preferably $C_5$–$C_7$, alkoxy, preferably $C_1$–$Cl_2$, thioalkoxy, preferably $C_1$–$C_4$, halogen, cyano, alkyl sulfonyl, preferably $C_1$–$C_6$, aryl sulfonyl, preferably phenyl sulfonyl, aryl, preferably phenyl, aryloxy, preferably phenoxy, or thioaryloxy, preferably thiophenoxy; and/or iii) aryl fused, preferably benzo, which is unsubstituted or mono- or independently polysubstituted by alkyl, preferably $C_1$–$C_{12}$, cycloalkyl, preferably $C_5$–$C_7$, alkoxy, preferably $C_1$–$C_{12}$, thioalkoxy, preferably $C_1$–$C_4$, halogen, preferably chloro and bromo, phenyl, phenoxy, or thiophenoxy, or iv) cycloalkyl fused, which is unsubstituted or mono- or independently polysubstituted by alkyl, preferably $C_1$–$C_8$, The preferred non-fused 1,4-, 1,5-, and 1,6-diols and 5–7 membered ring cyclic ether compounds, respectively, are i) unsubstituted, or ii) mono- or independently polysubstituted by alkyl, preferably $C_1$–$C_8$, aryl, preferably phenyl, which is unsubstituted or mono- or independently polysubstituted by alkyl, preferably $C_1$–$Cl_2$, cycloalkyl, preferably $C_5$–$C_7$, alkoxy, preferably $C_1$–$C_{12}$, thioalkoxy, preferably $C_1$–$C_4$, halogen, preferably chloro and bromo, phenyl, phenoxy or thiophenoxy. The most preferred 1,4-, 1,5-, and 1,6-diols and 5–7 membered ring cyclic ether compounds, respectively, are aryl substituted.

When having substitution by one or more aryl groups, one aryl substituent is preferably at the 1-position of the 1,4-, 1,5-, and 1,6-diol and in the 2-position of the 5–7 membered ring cyclic ether. The substituents on this aryl group preferably consist of any combination of alkyl or alkoxy including both straight and branched chain saturated hydrocarbyl moieties, preferably $C_1$–$C_{12}$, more preferably $C_1$–$C_8$, most preferably $C_1$–$C_4$. When the aryl group is phenyl which is i) monosubstituted, the substitution is preferably in the 4-position, or ii) polysubstituted, the substitution is preferably in any combinations of the 2-, 4-, or 6-positions. Examples of such phenyl substituents are 4-alkyl-, 2,4-dialkyl-, 2,4,6-trialkyl-, 4-alkoxy-, 2,4-dialkoxy-, 2,4,6-trialkoxy-, 2-alkyl-4-alkoxy-, 2-alkoxy-4-alkyl-, 2,6-dialkoxy-4-alkyl-, and 2,6-dialkyl-4-alkoxy-substituents.

The diols discussed above are preferably selected from the 1,4-diols, and the cyclic ethers are preferably selected from the tetrahydrofurans.

The preferred fused 1,4-, 1,5-, and 1,6-diols, or 5–7 membered ring cyclic ethers, respectively, are i) unsubstituted, or ii) mono- or independently polysubstituted by alkyl, preferably $C_1$–$C_8$, cycloalkyl, preferably $C_5$–$C_7$, vinyl, preferably in the 1-position, aryl, preferably phenyl, and iii) (2,3)-aryl fused, preferably (2,3)-benzo for the diols, or (3,4)-aryl fused, preferably (3,4)-benzo for the cyclic ethers.

Suitable di- and polyfunctional diols and cyclic ethers in this reaction can be selected from compounds of the general formula C-[B-C]$_w$, wherein w≧1, C independently represents the 1,4-, 1,5-, and 1,6-diols, tetrahydrofurans, tetrahydropyrans, or hexahydrooxepions, respectively, defined as above, and B independently represents alkylene which can be substituated, preferably $C_2$–$C_{20}$, for example ethylene, propylene, butylene, pentylene, hexylene; arylene, preferably phenylene, biphenylene or naphthylene; alkylenebisaryl, preferably metylenebifenyl; or aralkylene, preferably xylylene. The C to B attachment is preferably via the 1-position of the diol or via the 2-position of the cyclic ether.

Strong protonic acids which arc useful in this reaction can in principle be selected from any strong protonic acid. A strong acid (HX) is recognized by more or less complete dissociation in an aqueous solution to form a proton (H$^+$) and the corresponding base (X$^-$). Suitable strong protonic acids can be selected from: hydrohalogenic acids, such as hydrochloric, hydrobromic, and hydroiodic acid; perhalogenic acids, such as perchloric acid; tetrahaloboric acids, such as tetrachloroboric and tetrafluoroboric acid; hexahaloantimonic, -arsenic, and -phosphoric acids, such as hexachloroantimonic, hexafluoroantimonic, hexachloroarsenic, hexafluoroarsenic, hexachlorophosphoric, and hexafluorophosphoric acid; sulfonic and halogen-substituted alkyl or aryl sulfonic acids, such as p-toluensulfonic and triflic(trifluoromethane sulfonic)acid; phosphoric acid or sulfuric acid. Preferred strong protonic acids are perchloric, tetrafluoroboric, hexafluoroantimonic, hexafluoroarsenic, hexafluorophosphoric acid, p-toluensulfonic and triflic acid, most preferably tetrafluoroboric, hexafluoroantimonic, and hexafluorophosphoric acid.

In the production of a cyclic sulfonium salt compound having a non-nucleophilic anion, the strong protonic acid is preferably selected from tetrafluoroboric, hexafluoroantimonic, hexafluoroarsenic, or hexafluorophosphoric acid, most preferably hexafluoroantimonic or hexafluorophosphoric acid.

Since the corresponding base of the acid becomes the anion of the sulfonium salt compound, an ion-exchanging step is not necessary when using these preferred acids for producing a sulfonium salt compound having a non-nucleophilic anion. This results in a simplified one-step process.

When using commercial hexafluorophosphoric acid, stabilized by about 10% w/w of hydrogen fluoride, the reaction is preferably performed in a reaction vessel which not consists of glass, but preferably a vessel consisting of plastic materials or monel alloy, most preferably a polyolefinic materials such as polyethylene, polypropylene, or teflon.

The reaction can be carried out in an anhydrous protonic acid or a hydrous protonic acid solution. The term "protonic acid" refers to the strong protonic acids defined above. Preferably and conveniently the commercially available protonic acid solution is used, the concentration of which is dependent on the actual protonic acid. Examples of aqueous protonic acids are hexafluorophosphoric acid commercially available as 60% w/w solution, and hexafluoroantimonic acid available as the hydrate. HSbF$_6$.6H$_2$O. If desired, the anhydrous protonic acid, the hydrous protonic acid or the hydrous protonic acid solution can also be diluted with water to any convenient concentration, dependent on the actual protonic acid. More concentrated protonic acid solutions are however preferred since lower concentration will result in decreased overall reaction rate of the process. The concentration of aqueous protonic acid reactant is preferably at least 25%, more preferably at least 40%, or most preferably at least 50% w/w.

The reaction can be carried out in the presence or absence of an inert organic solvent. The presence of an inert organic solvent usually but not necessary leads to a two-phase system. Examples of such inert solvents are hydrocarbons, such as n-pentane, n-hexane, n-heptane, cyclohexane; aliphatic nitriles such as acetonitrile; dimethyl sulfoxide; and halogenated hydrocarbons, such as carbon tetrachloride, methylene chloride, chloroform, tetrachloro ethane, dichloro ethane, and ethylene dichloride. Of these, halogenated hydrocarbons, particularly methylene chloride, are preferred.

When an inert solvent is present in the reaction, the amount of the solvent can be varied depending on the type of solvent, the type and amount of the mercapto compound, strong protonic acid, and the diol/cyclic ether compound, etc. The amount of the solvent is preferably small since if the amount is too large, the overall reaction rate decreases. A preferred amount of solvent is less than about 2000, suitable about 200 ml per mole of the diol/cyclic ether compound.

The amount of the strong protonic acid the reaction is at least 0.5 equivalents (eq), more preferably at least 1.0 eq, most preferably at least 1.2 eq. and at most 10 eq, preferably at most 5 eq, most preferably at most 2 eq, based on the diol/cyclic ether compound. The amount of the mercapto compound in this reaction is at least 0.5 eq, preferably at least 0.9 eq, most preferably at least 1.0 eq, and at most 10 eq, preferably at most 5 eq, most preferably at most 2 eq, based on the diol/cyclic ether compound. The reaction can be carried out with equimolar amounts of the diol/cyclic ether compound and the mercapto compound with a slight excess of the protonic acid reactant. The relevant stochiometry of the reactants discussed herein refers to the reacting functional groups. Concequently, total conversion of, for example, 1 mole of a difunctional mercaptan (2 eq—SH) theoretically requires 2 moles of a monofunctional diol/cyclic ether and 2 moles of a protonic acid. The excess of acid required depends on the reactivity of the acid and the diol/cyclic ether compound. In some cases, an excess of the acid of 0.2 equivalents can be sufficient to carry the reaction to completion. However, use of larger excess of acid leads to higher reaction rate with almost no additional workup problems.

Since the diol/cyclic ether compound in most cases is the most expensive of the reactants, it is economically desirable to achieve high conversion of the diol/cyclic ether compound into the cyclic sufonium salt compound. This implies that the diol/cyclic ether compound should be the limiting component. It is, however, possible to reduce the amount of the mercapto compound to 1 equivalent relative to the diol/cyclic ether compound and still produce the sulfonium salt compound in high yield and purity. This is of great importance and value since minimizing the excess of the mercapto compound will, in addition to improved economy, decrease the bad smell, caused by unreacted mercapto compound, from the effluents from the workup. It is also possible to perform the reaction with less than 1 eq, for example 0.95 eq, of the mercapto compound, resulting in total conversion of the mercapto compound into the sulfonium salt compound, thus almost eliminating any mercaptan smell from the workup.

The reaction is preferably performed at a temperature from about 0° to about 70° C., more preferably from about 20° to about 50° C., particularily at room temperature. Higher reaction temperature may be useful in some cases due to sluggish reactants. Mixing the reactants require cooling due to exothermic ring-opening of the cyclic ether which is either added as a reactant or formed in situ from the corresponding diol. The temperature of the coolant should in some cases be subzero, lower than −10° C., more preferably lower than or equal to 0° C. most preferably lower than 10° C. The reaction can be performed at pressures ranging from sub-atmospheric pressure to super-atmospheric pressure, preferably at atmospheric pressure. Superatmospheric pressure may be caused by volatile or gaseous reactants such methylmercaptan or hydrochloric acid. The reaction can be performed under an air atmosphere. When long reaction times arc needed, the atmospheric oxidation of the mercaptan to a disulfide may be a problem. The oxidation can simply be avoided by performing the reaction under an inert gas atmosphere, preferably nitrogen or argon.

Some cyclic sulfonium salts of the invention are novel compounds per se. They all have benzylic substituents with respect to the sulfur atom, i.e. all are 2-aryl substituted. Such compounds are useful as latent thermal initiators for cationic polymerization, wherein the thermal latency primarily depends on the ability of the aryl substituent to stabilize positive charge at a benzylic position. The invention provides a tool for producing sulfonium salt initiators with improved solubility in polymerizable compounds which often are caracterized of hydrophobic and non-polar properties. The increased hydrophobicity was achieved by using long chain hydrocarbyl mercaptans, exemplified among the novel compounds per se. The flexibility of the reaction allows this fine tuning which constitutes a important technical contribution since solubility is problem associated with previously developed sulfonium salt initiators. Also, by the process of the invention, these novel compounds are produced in higher purity compared to previously known compounds of this type, leading to a more well-defined product and more uniform initiating characteristics.

The compounds which are novel per se are aryl-substituted or aryl-fused cyclic sulfonium salt compounds having the structural formula V, VI, and VII which are:

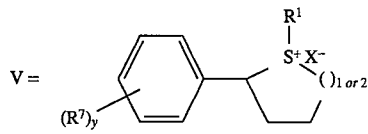

S-butyl-2-(phenyl)-tetrahydrothiophenium hexafluoroantimonate,

S-butyl-2-(4-methylphenyl)-tetrahydrothiophenium hexafluorophospate,

S-butyl-2-(4-methyoxyphenyl)-tetrahydrothiophenium hexafluoroantimonate,

S-dodecyl-2-(4-methylphenyl)-tetrahydrothiophenium hexafluorophosphate,

S-butyl-2-(4-methoxyphenyl)-tetrahydrothiophenium tetrafluroborate,

S-butyl-2-(4-methoxyphenyl)-tetrahydrothiophenium perchlorate,

S-butyl-2-(4-methoxyphenyl)-tetrahydrothiophenium triflate,

S-butyl-2-(4-isopropylphenyl)-tetrahydrothiophenium hexafluorophosphate,

S-butyl-2-(4-tert-butylphenyl)-tetrahydrothiophenium hexafluorophosphate,

S-butyl-2-(2,4-dimethylphenyl)-tetrahydrothiophenium hexafluorophosphate,

S-tert-butyl-2-(2,4-dimethylphenyl)-tetrahydrothiophenium hexafluorophosphate,

S-iso-butyl-2-(2,4-dimethylphenyl)-tetrahydrothiophenium hexafluorophosphate,

S-iso-propyl-2-(2,4-dimethylphenyl)-tetrahydrothiophenium hexafluorophosphate,

S-dodecyl-2-(2,4-dimethylphenyl)-tetrahydrothiophenium hexafluorophosphate,

S-phenyl-2-(2,4-dimethylphenyl)-tetrahydrothiophenium hexafluorophosphate,

S-butyl-2-(2,4-dimethylphenyl)-tetrahydrothiophenium hexafluoroantimonate,

S-butyl-2-(2-methyl-4-methoxyphenyl)-tetrahydrothiophenium hexafluorophosphate,

S-butyl-2-(2,4-dimethoxyphenyl)-tetrahydrothiophenium hexafluorophosphate,

S-butyl-2-(2,4,6-trimethylphenyl)-tetrahydrothiophenium hexafluorophosphate,

S-butyl-2-(2,6-dimethyl-4-methoxyphenyl)-tetrahydrothiophenium hexafluorophosphate, S-butyl-2-(4-methoxyphenyl)-pyranium hexafluorophosphate, S,S'-ethylene-1,2-bis[2-(4-methoxyphenyl)-tetrahydrothiophenium hexafluorophospate], S,S'-hexylene-1,6-bis[2-(4-methoxyphenyl)-tetrahydrothiophenium hexafluorophospate], S,S'-p-xylylene-bis[2-(4-methoxyphenyl)-tetrahydrothiophenium hexafluorophospate], and VI = 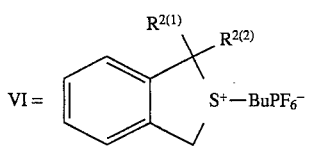

S-Butyl-2-phenyl-[3,4]-benzo-2,5-dihydro-thiophenium hexafluorophosphate,

S-Butyl-2-iso-propyl-[3,4]-benzo-2,5-dihydrothiophenium hexafluorophosphate,

S-Butyl-2,2-dimethyl-[3,4]-benzo-2,5-dihydrothiophenium hexafluorophosphate,

S-Butyl-2-metyl-2-phenyl-[3,4]-benzo-2,5-dihydrothiophenium hexafluorophosphate, S-Butyl-2,2-diphenyl-[3,4]-benzo-2,5-dihydrothiophenium hexafluorophosphate, and VII = 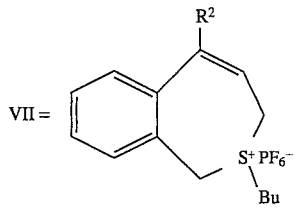

S -Butyl-5-methyl-[3,4]-benzo-2,7-dihydrothiepinium hexafluorophosphate,

S-Butyl -5-phenyl-[3,4]-benzo-2,7-dihydrothiepinium hexafluorophosphate.

Best mode of operation

The best mode of operation of the process according to the the present invention is to react an alkyl mercaptan, such as for example n-butyl-, iso-butyl-, sec-butyl-, or t-butyl mercaptan, with a 1-aryl substituted 1,4-diol or a 2-aryl substituted tetrahydrofuran, preferably the diol since the diols generally are more easily accessible, and a strong protonic acid, in which the corresponding base is non-nucleophilic. Examples of non-nuclephilic anions are: hexafluorophosphate, hexafluoroantimonate, hexafluoroarsenate, and tetrafluoroborate, preferably hexafluorophosphate and hexafluoroantimonate.

The aryl substituent is preferably phenyl, which is unsubstituted or mono- or independently polysubstituted by $C_1$–$C_4$ alkyl and/or $C_1$–$C_4$ alkoxy. Examples of such aryl substituens are phenyl, 4-methylphenyl, 4-methoxyphenyl, 2,4-dimethylphenyl, 2-methyl-4-methoxyphenyl, and 2,6-dimethyl-4-methoxyphenyl.

The reaction is performed by slowly adding aqueous $HPF_6$ (60% w/w, 1.5 eq) to an ice-cooled mixture of the diol (1.0 eq.) and the mercaptan (1.0 eq.). The reaction mixture is stirred (2–24 h) at room temperature (20°–30° C.) under a $N_2$-atmosphere. Then water (200 mL/mol diol) is added and the resulting slurry is filtrated. The crystals are washed with water (200 mL/mol in portions) and aqueous $NaHCO_3$ (100 mL/mol diol in portions). The crude material is recrystallized in ethanol (99.5%, 0.7–1 l/kg crude material).

DESCRIPTION OF THE FIGURES

The invention is illustrated by the enclosed FIGS. 1 and 2.

FIG. 1 clearly shows the transformation of 6f to the corresponding sulfonium salt S-butyl-2-(2,4-dimethylphenyl)-tetrahydthiophenium hexafluorophosphate 1f-(S-Bu)-$PF_6$ via the intermediate tetrahydrofuran 7f and sulfidoalcohol 8f. (For further experimental details, see examples 36 and 37). This means, as previously described herein, that either a diol or the corresponding cyclic ether can be used as one of the reactants in the reaction according to the process of the present invention. The transformation of the diol to the cyclic ether is momentaneous under the present conditions.

Figure 1:
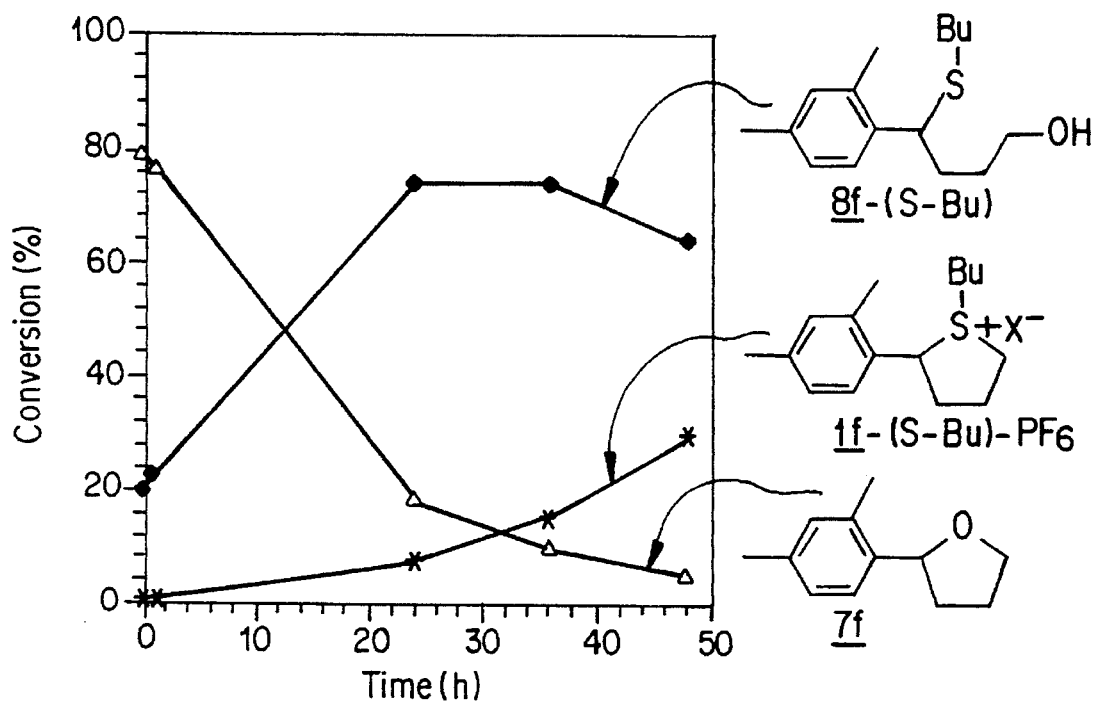
FIG. 1 shows the intermediates of the cyclization-reaction of 1-(2,4-dimethylphenyl)-1,4-butanediol 6f with n-butyl mercaptan in the presence of 31% w/w of $HPF_6$ at 25° C., as studied by $^1$H-NMR as the conversion vs time.
Figure 2:
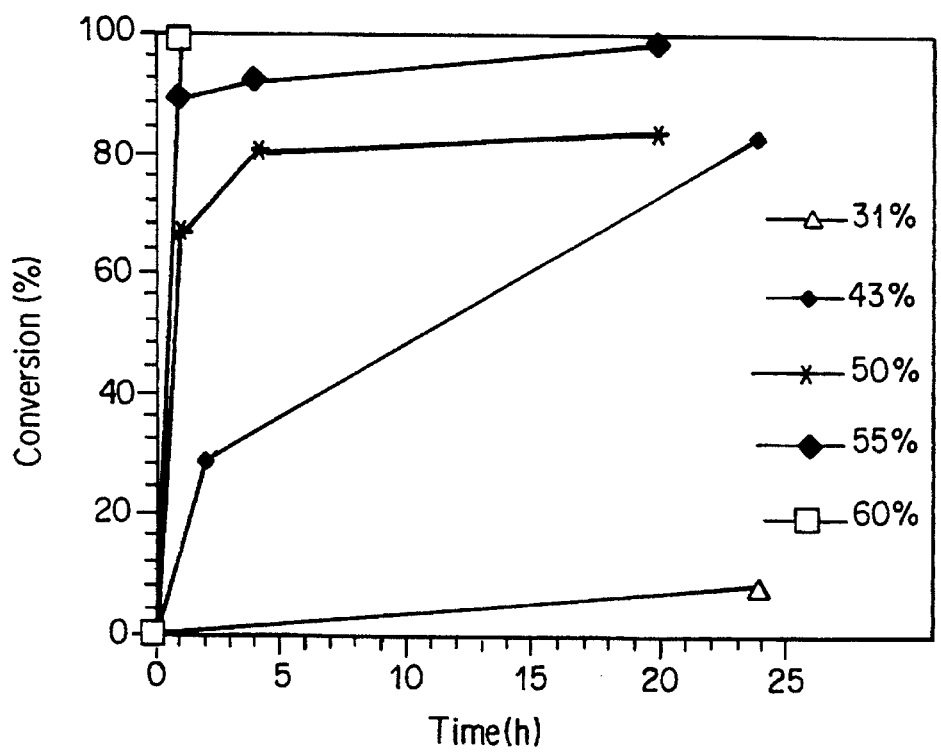
FIG. 2 shows how the rate of formation of 1f-(S-Bu)-$PF_6$ is affected by dilution of $HPF_6$ with water. As expected the overall reaction rate is very dependant on the proton activity. A two-fold dilution result in a 400-fold decrease of the reaction rate.

The process according to the invention is further demonstrated by the following examples. It should be understood that the examples are illustrative and not limitative. Percentage are given by weight unless otherwise specified.

EXAMPLES

The cyclic sulfonium salts synthesized using the process of this invention in the examples are of the general structures 1, 2, 3, 4, and 5.

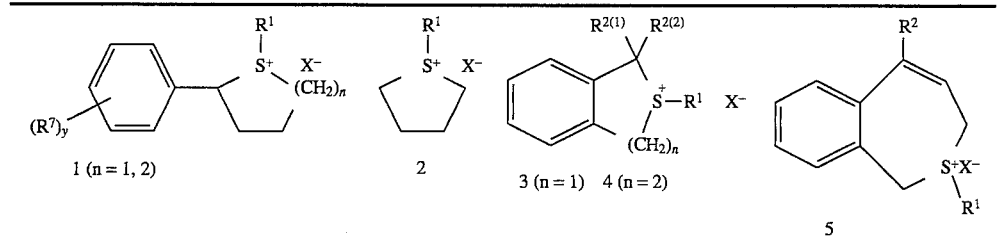

| | $(R^7)_y$ | | $R^{2(1)}$ | $R^{2(2)}$ | | $R^2$ |
|---|---|---|---|---|---|---|
| 1a | H | | 3A | H | H | 5A Me |
| 1b | 4-Me | | 3B | H | Ph | 5B Ph |
| 1c | 4-MeO | | 3C | H | i-Pr | |
| 1d | 4-i-Pr | | 3D | Me | Me | |
| 1e | 4-t-Bu | | 3E | Me | Ph | |

| | | | | |
|---|---|---|---|---|
| 1f | 2,4-diMe | n = 1 | 3F | Ph Ph |
| 1g | 2-Me, 4-MeO | | 4 | H  H |
| 1h | 2,4-diMeO | | For compounds 2–5 X = $PF_6$ | |
| 1i | 2,4,6-triMe | | and for 3–5 $R^1$ = n-Bu and | |
| 1j | 2,4-diMe-4-MeO | | for 2 $R^1$ = Benzyl | |
| 1k | 4-MeO (n = 2) | | | |

For compounds 1 $R^1$ = primary, secondary, and tertiary alkyl, phenyl, $-(CH_2)_2-$, $-(CH_2)_6-$, and p-xylylene Synthesis of cyclic sulfonium salts of type 1.

1-Aryl-1,4-butane-diols 6a–j and 1-(p-MeO-phenyl)-1,5-pentandiol 6k were transformed to S-alkyl-2-aryl-tetrahydrothiophenium salts 1 by reaction with a mercaptane in the presence of between 1.2–5 equivalents of the acid HX (where X=$PF_6$, $SbF_6$, $BF_4$, $ClO_4$, and $CF_3SO_3$). The reaction was performed at 25° C. or slightly above utilizing the commercial acid as the solvent or a two-phase system consisting of the commercial acid and methylene chloride. When using commercially hexafluorophosphoric acid, which is stabilized by approximative 10% w/w of hydrogen fluoride, the reactions were performed in polyethylene or polypropylene bottles. Utilizing glassflasks results in partial formation of sulfonium salts having fluorosilicates as the counter ion, see for example Christie et. al. J. Am. Chem. Soc. 1990, 112, 7619. The results are summarized in table 1. The salts 1 are crystallinic materials isolated as mixture of diastereomers typically in a 1:1.5 ratio. The workup was achieved by either diluting the reaction mixture with water followed by filtration of the crystallinic sulfonium salt or by extraction with methylene chloride. The reactions proceed very cleanly and usually yield pure crude products. Most of the salts however, are easily recrystallized from ethanol and in several cases crystallization afforded pure diastereomers where the transisomer precipitates first. The major diastereomer 1c(S-Me)-$PF_6$ was unambigously determined bye differential NOE-NMR techniques to the trans-isomer. Irradiaton of the Me-S group in the major isomer resulted in 21% enhancement whereas irraditon of the Me-S group in the minor gave less than 3% enhancement.

salts, see table 2. The reaction was also examined for a number of different mineral acids and the results are shown in table 3.

The mechanism (scheme 1) of the reaction is a multistep event and includes an immediate formation of the tetrahydrofuran derivative 7 which after protonation regioselectively reacts at the benzylic position to form the sulfido alcohol 8. The isomeric sulfidoalcohol 9 has not been observed in any of the cases we studied. The reaction can easily be followed by $^1$H-NMR and the methine protons on 6, 7, and 1 together with the methylene group $CH_2O$ in 8 are easily distinguished.

TABLE 1

| $(R^7)_y$ | Diol/Ether | Conditions[i] | Sulfonium salt | Yield % (trans/cis) |
|---|---|---|---|---|
| H | 6 a | A | 24 h 1a(S—Bu)—$PF_6$ | 94[ii] (1.8/) |
| H | 6 a | B | 60 h 1a(S—Bu)—$SbF_6$ | 82 [65][ii] (2.7/1) |
| 4-Me | 6 b | A | 24 h 1b(S—Bu)—$PF_6$ | 84 (1.4/1) |
| 4-MeO | 7 c | A | 24 h 1c(S—Bu)—$PF_6$ | 100 [78][ii] (6.7/1) |
| 4-MeO | 7 c | B | 24 h 1c(S—Bu)—$SbF_6$ | 82 [66][ii] (3.0/1) |
| 4-i-Pr | 6 d | A | 24 h 1d(S—Bu)—$PF_6$ | 58 (1.5/1) |
| 4-t-Bu | 6 e | A | 24 h 1e(S—Bu)—$PF_6$ | 51 (2/1) |
| 2,4-diMe | 7 f | A | 17 h 1f(S—Bu)—$PF_6$ | 100 [70][ii] (1/1) |
| 2,4-diMe | 6 f | B | 24 h 1f(S—Bu)—$SbF_6$ | 69 [51][ii] (4/1) |
| 2-Me, 4-MeO | 6 g | A | 17 h 1g(S—Bu)—$PF_6$ | 76 [42][ii] (1.7/1) |
| 2,4-diMeO | 6 h | A | 16 h 1h(S—Bu)—$PF_6$ | 66 (3.7/1) |
| 2,4,6-triMeO | 6 i | A | 24 h 1i(S—Bu)—$PF_6$ | 59 (>10/1) |
| 2,6-diMe, 4-MeO | 6 j | A | 4 h 1j(S—Bu)—$PF_6$ | 98 [43][ii] (>10/1) |
| 4-MeO | 6 k | A | 120 h 1k(S—Bu)—$PF_6$ | 32 (>10/1)[iii] |

[i]Conditions A: BuSH (1.4–1.5 eq), acid (1.4–2.0 eq), CH2Cl2 (0.2–1 mL/mmol 2); Conditions B: BuSH (1.0 eq), acid (2.0 eq).
[ii]Yield after one recrystallization in EtOH.
[iii]The reaction was quenched after 52% conversion and the salt was accompanied with 5-(4-MeO-Phenyl)-5-BuS-pentan-1-ol.

The reaction is general with respect to the substituent $R^1$ including dimercaptans allowing synthesis of bis-sulfonium

Scheme 1

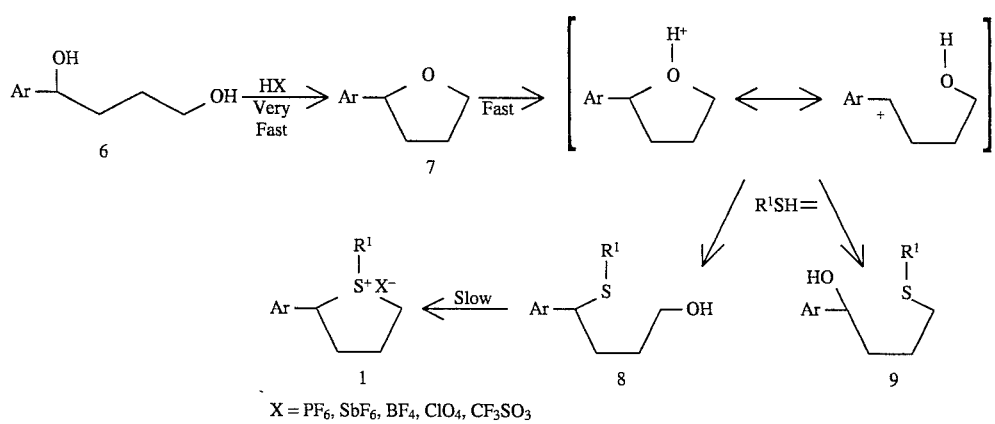

X = PF$_6$, SbF$_6$, BF$_4$, ClO$_4$, CF$_3$SO$_3$

Synthesis of the diols 6 was achieved by a two-step procedure, scheme 2, These methods are literature procedures starting with AlCl$_3$-catalyzed Friedel-Crafts acylation of the appropriate aromatic compound 10 with succinic anhydride or glutaric anhydride to form the ω-aroyl-carboxylic acids 11, see Olah, G. A. *Friedel-Crafts Chemistry* John Wiley 1973 91 ff and Olah, G. A. Friedel-Crafts and Related Reactions John Wiley 1964, 3, 551 ff; Tamura, Y. Yakura, T., Yoshiaki, Y, Haruta, *J. Chem. Pharm. Bull.* 1985, 33, 1097.

Friedel-Crafts acylations are often performed in solvents such as nitrobenzene, CS$_2$, and chlorinated hydrocarbons. We have used the aromatic hydrocarbon 10 as the solvent for the acylation, see Fieser, L. F. and Seligman, A. M. *J. Am. Chem. Soc.* 1938, 60, 170. The acids 11 were then reduced to the diols 6 with LiAlH$_4$ applying standard methodology, see for example Fieser. L. F. and Fieser, M. *Reagents for Organic Synthesis* John Wiley 1967, 1,584.

Scheme 2

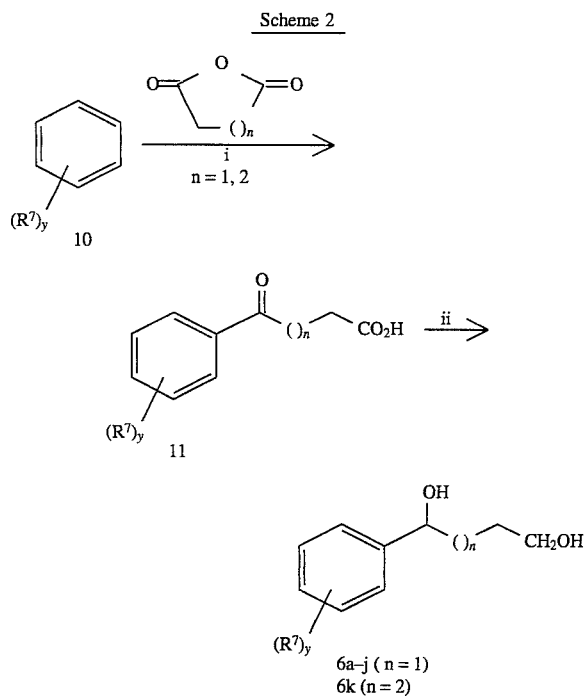

i) AlCl$_3$(2eq), 10(5.5eq), 25° C., 6h.
ii) LiAlH$_4$(1.5eq), THF, 8h

Synthesis of benzofused cyclic sulfonium salts of type 3, 4 and 5.

Substituted benzenedimethanols 12 and 13 reacted smoothly with BuSH (n-butylmercaptan=n-butanethiol) in hexafluorophosphoric acid to the sulfonium salts 3, 4, and 5, see eqation 3. The results are summarized in table 4.

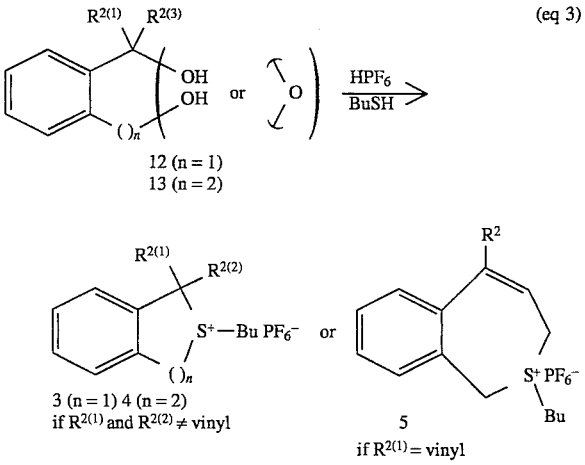

(eq 3)

The diols 12 were synthesized via a general organometallic route starting from phthalide, eq 4. Grignard reagents were utilized for preparation of compounds 12 ($R^{2(1)}=R^{2(2)}$) analogously to the procedures reported in: Smith, J. G. and Wikman, R. T. Tetrahedron 1974, 30, 2603 and Rickborn, B et. al. *J. Org. Chem.* 1989, 54, 4253. The diols 8 ($R^{2(1)}\neq R^{2(2)}$) were prepared by mono addition of an organolithium compound to ftalid followed by reaction with a grignard reagent ($R^{2(2)}\neq H$) or LiAlH$_4$ ($R^{2(2)}=H$). These two steps were performed in a one-pot procedure. Mono addition of R-Li to lactones to form lactoles have been shown previously, see for example Rickborn, Bet. al. *J. Org. Chem.* 1989, 54, 4253 and Bihovsky, R. and Rosenblum, S. B. *J. Am. Chem. Soc.* 1990, 112, 2746.

TABLE 2

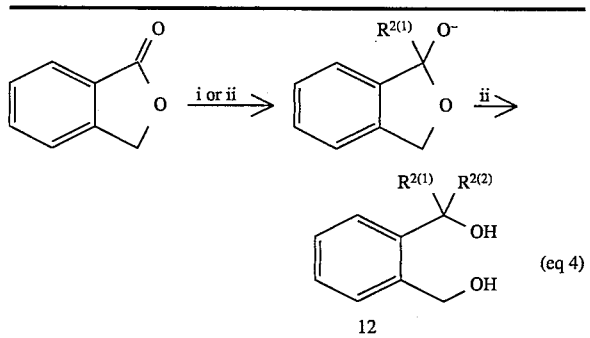

i) $R^{2(1)}Li$, THF, $-78°$ C., 1 h.
ii) $R^{2(2)}MgX$, THF, RT or LAH for $R^{2(2)} = H$ Synthesis of 1f-PF$_6$ and 1c-PF$_6$ by variation of the mercaptan[a]

| Mercaptan | Reaction time[b] | Yield % (trans/cis) |
|---|---|---|
| n-Butylmercaptan[c] | 1 h | 95 (1.5/1) |
| n-Dodecylmercaptan[c] | 20 h | 73 (1.6/1) |
| i-Butylmercaptan[c,d] | 24 h | 94 (1.2/1) |
| i-Propylmercaptan[c,d] | 24 h | 87 (6.0/1) |
| t-Butylmercaptan[c,d] | 5 h | 96 (>39/1) |
| Phenylmercaptan[c,e] | 100 h | 88 (2/1) |
| 1,2-Dimercaptoethane[f,g] | 1 h | 99 |
| 1,6-Dimercaptohexane[f,g] | 2 h | 83 |
| p-Xylylene-α,α'-dithiol[f,g] | 4 h | 86 |

[a]The reactions were performed in aqueous HPF$_6$ (60% w/w; 1.5 eq) at 25° C. using 1.0 eq of mercaptan relative to the diol 6f.
[b]Refers to the time to workup.
[c]The product was a 1f-PF$_6$ sulfonium salt.
[d]>95% conversion after 1 h.
[e]65% conversion after 0.5 h.
[f]The cyclic ether 7c was used. The bis-salts are a mixture of theoretically 8 diastereomers.
[g]The product was a 1c-PF$_6$ sulfonium salt.

TABLE 3

Synthesis of 1c(S—Bu)—X from 7c by variation of the acid (HX)[a]

| HX | ([H$^+$])[b] | Conditions[c] | Yield % (trans/cis) |
|---|---|---|---|
| HPF$_6$ | (60%, 7.4M) | 3 h, 25° C.[d,g] | 95 (1.5/1) |
| HSbF$_6$·6H$_2$O | (5.8M) | 20 h, 50° C.[e] | 95 (5.3/1) |
| HBF$_4$ | (50%, 7.6M) | 23 h, 50° C.[f,g] | 88 (2.2/1) |
| HClO$_4$ | (70%, 10.5M) | 24 h, 25° C. | 95 (2/1) |
| CF$_3$SO$_3$H | (98%, 3.9M) | 24 h, 50° C. | 95 (2/1) |

[a]The reactions were performed in aqueous HX (1.5 eq) using 1.0 eq of BuSH relative to the ether 7c.
[b]Formal molarity of the commercial acid HX.
[c]Refers to the time to workup.
[d]89% conversion after 1 h.
[e]65% conversion after 0.5 h.
[f]72% conversion after 24 h.
[g]The diol 6c was employed as the starting material.

TABLE 4

Synthesis of the benzo-fused sulfonium salts 3, 4, and 5.

| $R^{2(1)}$ | $R^{2(2)}$ | Diol | Conditions[a] | Product | Yield % |
|---|---|---|---|---|---|
| H | H | 12A | 66 h | 3A | 56 |
| H | Ph | 12B | 7 h | 3B | 69[b] |
| H | i-Pr | 12C | 6 h | 3C | 38[c] |
| Me | Me | 12D | 50 h | 3D | 43 |
| Me | Ph | 12E | 4.5 h | 3E | 73 |
| Ph | Ph | 12F | 22 h | 3F | 60 |
| vinyl | Me | 12G | 6 h | 5A | 47 |
| vinyl | Ph | 12J | 5.5 h | 5B | 60 |
| H | H | 13 | 9 d | 4 | 85 |

TABLE 4-continued

Synthesis of the benzo-fused sulfonium salts 3, 4, and 5.

| $R^{2(1)}$ | $R^{2(2)}$ | Diol | Conditions[a] | Product | Yield % |
|---|---|---|---|---|---|

[a]Conditions: BuSH (2.0 eq), HPF6 (3.5 eq) reactions were performed at 25° C. and worked up after the time shown in the table.
[b]The crude product contained 8% of 3a and was 2.2/1 mixture of diastereomers.
[c]The product was obtained as 3.3/1 mixture of two diastereomers.
[d]The starting material was isochromane 13.

Experimental section including examples

General

NMR-spectra were recorded on a 200 MHz Bruker ACE spectrometer equipped with a $^1$H/$^{13}$C-dual probe. Shifts are reported in ppm δ units relative to tetramethylsilane (internal standard) and were recorded in CDCl$_3$ not otherwise noted. Melting points were recorded on a Electrothermal Digital Melting Point Apparatous and are uncorrected. IR spectra were obtained with a Perkin Elmer 1760 (FTIR) spectrometer. HPF$_6$ (60% in H$_2$O) and HSbF$_6$·H$_2$O came from Ozark-Mahoning (Tulsa, Okla., 74107 U.S.A.). HBF$_4$ (48% in H$_2$O), glutaric anhydride (98%), BuSH and MeMgCl (2M in diethylether) came from Merck. 3-Benzoylpropionic acid (11a), 2-(Hydroxymethyl)-benzylalcohol (12a) and all other chemicals were purchased from Aldrich Chemical Co. The cyclization reactions were performed in screwcapped polypropylene plastic bottles. Elemental analysis were performed by Mikrokemi AB, Uppsala, Sweden. The following abbreviations have been used: milliliter=mL, equivalents= eq. grams=g, tetrahydrofuran=THF.

General procedure for synthesis of sulfoniumsalts of type 1.

General procedure A

The acid (1.2–4.0 eq) was added slowly to an ice-cooled solution of diol or cyclic ether (1 eq) and BuSH (1.0–1.5 eq) in CH$_2$Cl$_2$ (200–1000 mL/mol diol). The reaction mixture was stirred at the indicated time and temperature under a N$_2$-atmosphere. Water (200–1000 mL/mol diol) was added, the layers were separated and the aqueous-layer was extracted with CH$_2$Cl$_2$ (typically 3×50 mL/mol diol). The combined organic layers were washed with water (typically 100 mL/mol diol) and aqueous NaHCO$_3$ (saturated, 100 mL/mol diol), then dried (MgSO$_4$) and concentrated by rotary evaporation. Crude crystallinic products were recrystallized in EtOH (99.5%, 0.7–1 L/kg crude material). Sulfonium salt obtained as oils were purified by: dissolving the crude oil in a small volume of CH$_2$Cl$_2$ and extracted 5–10 times with petroleumether (5 times the CH$_2$Cl$_2$ volume). Traces of mercaptan the product was removed by washing with a H$_2$O$_2$-solution [H$_2$O$_2$ (35% w/w)/NaOH (2M) 1:4].

General procedure B

The reaction is performed by slowly adding the acid (1.2–4.0 eq) to an ice-cooled mixture of the diol (1.0 eq) and the mercaptan (1.0 eq). The reaction mixture is stirred at the indicated time and temperature (20°–50° C.) under a N$_2$-atmosphere. Then water (200 mL/mol diol) is added and the resulting slurry is filtrated. The crystals are washed with water (200 mL/mol in portions) and aqueous NaHCO$_3$ (100 mL/mol diol in portions). The crude material is recrystallized in ethanol (99.5%, 0.7–1 l/kg crude material).

Example 1

S-Butyl-2-(phenyl)-tetrahydrothiophenium hexafluorophosphate [1a(S-Bu)-PF$_6$]

The diol 6a (415.5 g, 2.5 mol) was reacted with BuSH (316g. 3.5 mol) and aqueous HPF$_6$ (60%, 912 g, 3.75 g) in CH$_2$Cl$_2$ (550 mL) for 24 h at RT (room temperature). Workup according to the general procedure A and recrystallization in EtOH (700 mL) gave 860 g (94%) white crystals of 1a(S-Bu)-PF$_6$ as a 1.8/1 mixture of diastereomers. Mp: 75°–80° C. $^1$H-NMR (aceton-d$_6$): 7.75–7.40 (m, Ar—H); 5.61 (dd, 1H, J=12.5 and 5.3 Hz, S—CH, minor isomer); 5.32 (dd, 1H. J=10.4 and 6.5 Hz, S—CH, major isomer); 4.19–4.02 (m, CH$_2$—S); 3.92–3.58 (m, CH$_2$—S); 3.25–2.30 (m, CH—CH$_2$—CH$_2$); 2.00–1.80 (m, CH$_2$—CH$_2$—CH$_3$); 1.58–1.15 (m, CH$_2$-CH$_3$); 0.91 (t, 3H, J=7.3 Hz, CH$_3$, major isomer); 0.72 (t, 3H, J=7.2 Hz, CH$_3$, minor isomer). $^{13}$C-NMR (aceton-d$_6$): 135.30; 130.69; 130.02; 129.92; 129.79; 128.80; 68.02; 64.65; 45.50; 44.30; 43.34; 39.10; 38.42; 31.47; 29.37; 28.05; 27.41; 27.11; 21.67; 13.17; 13.03; Anal. Calcd for C$_{14}$H$_{21}$SPF$_6$: C, 45.90; H, 5.78; S, 8.75 Found: C, 45.8; H, 5.8; S, 8.2.

Example 2

S-Butyl-2-(phenyl)-tetrahydrothiophenium hexafluroantimonate [1a(S-Bu)-SbF$_6$]

HSbF$_6$.6H$_2$O (876.5 g, 2.5 mol) was added to a mixture of diol 6a (208 g, 1.25 mol) and BuSH (135 mL, 1.25 mol) kept at 10° C. The reaction temperature was raised to 50° C. and the mixture was stirred for 60 h. H$_2$O (300 mL) was added and two layers were formed. The aqueous-layer (+100 mL H$_2$O) was extracted with CH$_2$Cl$_2$ (2×100 mL). CH$_2$Cl$_2$ (400 mL) was added to the organic layer and the layer was washed with H$_2$O (100 mL), Aqueous NaHCO3 (sat., 3×100 mL) and dried (MgSO$_4$). Evaporation gave 467.3 g (82%). Recrystallisation in EtOH (2.6 L) gave 369 g (65%) of white crystals 1a(S-Bu)-SbF$_6$ as a 2.7/1 mixture of diastereomers. Mp: 57.2°–59.1° C. $^1$H-NMR: Major isomer 7.43 (s, 5H, Ar—H); 5.01 (dd, 1H, J=11.3 and 5.6 Hz, CH—S); 3.86–3.73 (m, 1H, S—CH$_2$); 3.63–3.52(m, 1H, S—CH$_2$); 3.40 (t, 2H, J=8 Hz, S—CH$_2$CH$_2$); 2.90–2.29 (m, 4H, CH$_2$); 1.84–1.69 (m, 2H, CH$_2$); 1.52–1.35 (m, 2H, CH$_2$); 0.89 (t, 3H, J=7.3 Hz, CH$_3$); Minor isomer (distinguishable peaks in mixture with major isomer) 7.49 (s, 5H, Ar—H); 5.34 (dd, 1H, J=11.3 and 5.6 Hz, CH—S); 4.02–3.89 (m, 1H, S—CH$_2$); 1.30–1.17 (m, 2H, CH$_2$); 0.72 (t, 3H, J=7.1 Hz, CH$_3$). $^{13}$C-NMR: major isomer 132.91; 129.92; 129.73; 127.89; 68.97; 43.81; 43.50; 38.74; 28.87; 27.15; 21.40; 13.11; Minor isomer 130.82; 129.82; 129.24; 127.55; 65.30; 44.90; 38.64; 31.17; 28.06; 26.64; 21.34; 13.00. IR: 1462; 1233; 730; 703; 659 cm$^{-1}$. Anal. Calcd for C$_{14}$H$_{21}$SSbF$_6$: C, 36.79; H, 4.63; S, 7.01. Found: C, 36.9; H, 4.7; S, 7.1.

Example 3

S-Butyl-2-(4-methylphenyl)-tetrahydrothiophenium hexafluorophosphate [1b(S-Bu)-PF$_6$]

Aqueous HPF$_6$ (60%, 94.6 g, 0.39 mol) was added slowly to a mixture of diol 6b (50 g, 0.28 mol) and BuSH (25.06 g, 0.28 mol) kept at 0° C. and under N$_2$-atmosphere. The reaction mixture was stirred for 24 h at 25° C. H$_2$O (500 mL) and CH$_2$Cl$_2$ (100 mL) was added and the layers were separated. The aqueous-layer was extracted with CH$_2$Cl$_2$ (2×20 mL). The combined organic layers were washed with aqueous NaHCO3 (sat., 2×20 mL) and dried (MgSO$_4$). Evaporation gave 89 g (84%) colorless oil of 1b(S-Bu)-PF$_6$ as a 1.4/1 mixture of diastereomers. $^1$H-NMR: Major isomer 7–34–7.19 (m, 4H, Ar—H); 5.04 (dd, 1H, J=11.1 and 6.3 Hz, CH—S); 3.88–3.75 (m, 1H, CH$_2$—S); 3.70–3.57 (m, 1H, CH$_2$—S); 3.45 (t, 2H, J=7.5 Hz, S—CH$_2$CH$_2$); 2.89–2.78 (m, 1H, CH$_2$); 2.68–2.49 (m, 2H, CH$_2$); 2.49–2.22 (m, 1H, CH$_2$); 2.35 (s, 3H, CH$_3$—Ar); 1.85–1.65 (m, 2H, CH$_2$); 1.50–1.32 (m, 2H, CH$_2$); 0.89 (t, 3H, J=7.2 Hz, CH$_3$); Minor isomer (distinguishable peaks in mixture with major isomer) 5.50 (dd, 1H, CH—S); 2.37 (s, 3H, CH$_3$—Ar); 0.73 (t, 3H, CH$_3$). $^{13}$C-NMR: Major isomer 140.00; 130.28 (2C); 129.95; 127.81 (2C); 66.72; 43.83; 43.18; 38.64; 28.71; 27.14; 21.34; 21.18; 13.13; Minor isomer (distinguishable peaks in mixture with major isomer) 141.05; 130.37 (2C); 129.12 (2C); 124.58; 65.20; 45.56; 38.23; 31.20; 27.91; 26.62; 21.09: 13.06.

Example 4

S-Butyl-2-(4-methoxyphenyl)-tetrahydrothiophenium hexafluorophosphate [1c(S-Bu)-PF$_6$]

The cyclic ether 7c (601 g, 3.37 mol) was reacted with BuSH (426 g, 4.72 mol) and aqueous HPF$_6$ (60%, 1.23 kg, 5.05 mol) in CH$_2$Cl$_2$ (750 mL) for 24 h. Workup according to the general procedure A gave 1.33 kg (100%) of crude 1c(S-Bu)-PF$_6$ as a 1.5/1 mixture of diastereomers. Recrystallisation in EtOH (1 L) gave 1.038 kg (78%) white crystals of 1c(S-Bu)-PF$_6$ as a 6.7/1 mixture of diastereomers. Mp: 83.7° C. $^1$H-NMR: Major isomer 7.38 (d, 2H, J=8.8 Hz, Ar); 6.91 (d, 2H, J=8.8 Hz, Ar); 5.08 (dd, 1H, J=11 and 6 Hz, CH—S); 4.0–3.7 (m, 1H, CH$_2$—S); 3.80 (s, 3H, MeO); 3.65–3.5 (m, 1H, CH$_2$—S); 3.42 (t, 2H, J=7.2 Hz. S—CH$_2$CH$_2$CH$_2$CH$_3$), 2.9–2.25 (m, 4H, CH$_2$); 1.75 (m, 2H, CH$_2$); 1.43 (m, 2H, CH$_2$); 0.89 (t, 3H, J=7.3 Hz, CH$_3$); Minor isomer 7.43 (d, 2H, J=8.8 Hz, Ar); 6.95 (d, 2H J=8.8 Hz, Ar); 5.38 (dd, 1H, J=11 and 6 Hz, CH$_2$—S); 4.0–3.7 (m, 1H, CH$_2$—S); 3.83 (s, 3H, MeO); 3.65–3.5 (m, 1H, CH$_2$—S); 3.42 (t, 2H, J=7.2 Hz, S—CH$_2$CH$_2$ CH$_2$CH$_3$), 2.9–2.25 (m, 4H, CH$_2$); 1.5–1.0 (m, 4H, CH$_2$); 0.75 (t, 3H, J=7.3 Hz, CH$_3$). $^{13}$C-NMR: Major isomer 160.64; 129.38 (2C); 124.55; 114.99 (2C); 69.05; 55.37; 43.43; 43.08; 38.49; 28.64; 27.15; 21.35; 13.14; Minor isomer 161.29; 130.68 (2C); 119.19; 115.05 (2C); 65.61; 55.43; 44.49; 38.17; 31.45; 27.93; 26.64; 21.35; 13.08. IR (KBr, major+minor isomer): 1518; 1260; 1186; 832 (PF$_6$$^{-1}$) cm$^{-1}$. Anal. Calcd for C$_{15}$H$_{23}$OSPF$_6$: C, 45.45; H, 5.85; S, 8.09.Found: C, 45.3; H, 5.9; S, 7.7.

Example 5

S-Butyl-2-(4-methoxyphenyl)-tetrahydrothiophenium hexafluorophosphate [1c(S-Bu)-PF$_6$]

The diol 6c was reacted with BuSH (1 eq) and aqueous HPF$_6$ (60%, 1.5 eq) at 25° C. for 3 h according to procedure B. Extractive workup with CH$_2$Cl$_2$ according to procedure A afforded 95% of 1c(S-Bu)-PF$_6$ as a 1.5/1 mixture of diastereomers.

Example 6

S-Butyl-2-(4-methoxyphenyl)-tetrahydrothiophenium hexafluoroantimonate [1c(S-Bu)-SbF$_6$]

HSbF$_6$.H$_2$O (106 g, 307.5 mmol) was added slowly to an ice-cooled solution of cyclic ether 7c (27.4 g, 153.7 mmol) and BuSH (16.5 mL, 153.7 mmol). The temperature was raised to 50° C. and the reaction mixture was stirred for 24 h. H$_2$O (50 mL) and CH$_2$Cl$_2$ (50 mL) was added and the layers were separeted. The aqueous-layer was extracted with CH$_2$Cl$_2$ (2×40 mL). The combined organic layers were washed with aqueous NaHCO$_3$ (sat., 2×50 mL) and dried (MgSO$_4$). Evaporation gave 61.6 g (82%) of 1c(S-Bu)-SbF$_6$ as a colorless oil that crystallized slowly (diastereomer mixture 2.5/1). Recrystallization in EtOH (50 mL) gave 49.4 g (66%) white crystals of 1c(S-Bu)-SbF$_6$ as a 3/1 mixture of diastereomers. Mp: 75°–77.1° C. $^1$H-NMR: Major isomer 7.37 (d, 2H, J=8.8 Hz, Ar—H); 6.93 (d, 2H, J=8.8 Hz, Ar—H); 5.00 (dd, 1H, J=11.0 and 6.2 Hz, S—CH); 3.86– 3.69 (m, 1H, S—CH$_2$); 3.80 (s, 3H, OCH$_3$); 3.59–3.49 (m, 1H, S—CH$_2$); 3.43–3.34 (m, 2H, S—CH$_2$); 2.84–2.26 (m, 4H, CH$_2$); 1.85–1.69 (m, 2H, CH$_2$); 1.55–1.35 (m, 2H, CH$_2$); 0.90 (t, 3H, J=7.2 Hz, CH$_3$); Minor isomer (distinguishable peaks in mixture with major isomer) 7.43 (d, 2H, Ar—H); 6.96 (d, 2H, Ar—H); 5.33 (dd, 1H, J=11.7 and 6.0 Hz; S—CH); 3.82 (s, 3H, OCH$_3$); 0.75 (t, 3H, J=7.3 Hz, CH$_3$). $^{13}$C-NMR: Major isomer 160. 72; 129.35 (2C); 1124.29, 115.06 (2C); 69.47; 55.38; 43.51; 43.31; 38.46; 28.73; 27.19; 21.38; 13.11; Minor isomer 161.37; 130.69 (2C); 118.95; 115.12 (2C); 65.47; 55.44; 44.65; 31.53; 28.09; 26.64; 21.41; 13.05. IR: 1612; 1517; 1469; 1258; 1233; 1185; 1029; 834; 655 cm$^{-1}$. Anal. Calcd for C$_{15}$H$_{23}$OSSbF$_6$: C, 36.98; H, 4.76; S, 6.58. Found: C, 37.0; H, 4.8; S, 6.6.

Example 7

S-Butyl-2-(4-methoxyphenyl)-tetrahydrothiophenium hexafluoroantimonate [1c(S-Bu)-SbF$_6$]

The cyclic ether 7c was reacted with BuSH (1 eq) and HPSb$_6$.6H$_2$O (1.5 eq) at 50° C. for 20 h according to procedure B. Extractive workup with CH$_2$Cl$_2$ according to procedure A afforded 95% of 1c(S-Bu)-SbF$_6$ as a 5.3/1 mixture of diastereomers.

Example 8

S-Dodecyl-2-(4-methoxyphenyl)-tetrahydro-thiophenium hexafluorophosphate [1c(S-dodecyl)-PF$_6$]

Aqueous HPF$_6$ (60%, 7.3 g, 30 mmol) was added slowly to a solution of diol 6c (2.94 g, 15 mmol) and 1-dodecylmercaptan [1-dodecanthiol] (4.55 g, 22.5 mmol) in CH$_2$Cl$_2$ (20 mL). The reaction mixture was stirred for 24 h. Workup according to the general procedure A gave 3.79 g (50%) of 1c(S-dodecyl)-PF$_6$ as a 2/1 mixture of diastereomers. $^1$H-NMR: 7.53–7.45 (dd, 2H, Ar—H); 6.95 (t, 2H, Ar—H); 5.45 (dd, 1H, CH—S, minor isomer); 5.20 (dd, 1H, CH—S, major isomer); 4.08–3.44 (m, 4H, CH$_2$—S); 3.83 (s, 3H, OCH$_3$, minor isomer); 3.81 (s, 3H, OCH$_3$, major isomer); 3.05–2.55 (m, 4H, CH—CH$_2$—CH$_2$—S); 1.87–1.7 (m, CH$_2$); 1.5–0.9 (m, 20H, CH$_2$); 0.87 (t, 3H, CH$_3$—CH$_2$);

Example 9

S-Butyl-2-(4-methoxyphenyl)-tetrahydrothiophenium tetrafluoroborate [1c(S-Bu)-BF$_4$]

Aqueous HBF$_4$ (50%, 8.23 g, 45 mmol) was added to a mixture of diol 6c (5.89 g, 30 mmol) and BuSH (2.71 g, 30 mmol). The reaction mixture was stirred for 3 h at RT and for 20 h at 50° C. CH$_2$Cl$_2$ (10 mL) was added and the layers were separated. The aqueous-layer was extracted with CH$_2$Cl$_2$ (10 mL). The combined organic layers were washed with aqueous NaHCO$_3$ (sat., 10 mL), H$_2$O (5 mL) and dried (MgSO$_4$). Evaporation gave 8.91 g (88%) of 1c(S-Bu)-BF$_4$ as a 2.2/1 mixture of diastereomers. $^1$H-NMR: Major isomer 7.43 (d, 2H, Ar—H); 6.91 (d, 2H, Ar—H); 5.22 (dd, 1H, CH—S); 4.05–3.40 (m, 7H, including CH$_2$—S(ring), 2H, 3.80 (s, 3H, CH$_3$O), and 3.50 (t, 2H, CH$_2$S)); 3.06–2.20 (m, 4H, CH$_2$ (ring)); 1.78 (m, 2H, CH$_2$CH$_2$CH$_3$); 1.44 (m, 2H, CH$_2$CH$_3$); 0.89 (t, 3H, CH$_2$CH$_3$); Minor isomer (distinguishable peaks in mixture with major isomer) 7.48 (d, Ar—H); 6.95 (d, Ar—H); 5.47 (dd, CH$_2$—S); 3.82 (s, CH$_3$O); 0.75 (t, CH$_2$CH$_3$). $^{13}$C-NMR: Major isomer 160.47; 129.50 (2C); 124.97; 114.85 (2C); 68.54; 55.32; 43.57; 42.99; 8.54; 28.59; 27.18; 21.35; 13.18; Minor isomer (distinguishable peaks in mixture with major isomer) 161.13; 130.76 (2C); 119.62; 114.90 (2C); 65.36; 55.39; 44.53; 37.90; 31.48; 7.92; 26.69; 21.35; 13.11.

Example 10

S-Butyl-2-(4-methoxyphenyl)-tetrahydrothiophenium perchlorate [1c(S-Bu)-ClO$_4$]

Aqueous HClO$_4$ (70%, 2.153 g, 15 mmol) was added to a mixture of cyclic ether 7c (1.782 g, 10 mmol) and BuSH (0.902 g, 10 mmol). The temperature was raised to 50° C. and the reaction mixture was stirred for 24 h. H$_2$O (5 mL) and CH$_2$Cl$_2$ (10 mL) was added and the layers were separated. The aqueous-layer was extracted with CH$_2$Cl$_2$ (2×5 mL). The combined organic layers were washed with aqueous NaHCO$_3$ (sat., 5 mL), H$_2$O (5 mL) and dried (MgSO$_4$). Evaporation gave 3.34 g (95%) oil of 1c(S-Bu)ClO$_4$ as a 2/1 mixture of diastereomers. $^1$H-NMR: Major isomer 7.42 (d, 2H, Ar—H); 6.93 (d, 2H, Ar—H); 5.27 (dd, 1H, CHS); 4.10–3.50 (m, 7H, including CH$_2$S (ring), 2H, 3.81 (s, 3H, CH$_3$O), and 3.57 (t, 2H, CH$_2$S)); 3.10–2.30 (m, 4H, CH$_2$(ring)); 2.80 (m, 2H, CH$_2$CH$_2$CH$_3$); 1.47 (m, 2H, CH$_2$CH$_3$); 0.91 (t, 3H, CH$_2$CH$_3$); Minor isomer (distinguishable peaks in mixture with major isomer) 7.48 (d, Ar—H); 6.97 (d, ArH); 5.51 (dd, CHS); 3.83 (s, CH$_3$O); 1.25 (m, CH$_2$CH$_3$); 0.76 (t, CH$_2$CH$_3$). $^{13}$C-NMR: Major isomer 160.41; 129.41 (2C); 124.73; 114.80 (2C); 68.52; 55.26; 43.71; 43.07; 38.53; 28.66; 7.13; 21.31; 13.06; Minor isomer (distinguishable peaks in mixture with major isomer) 161.05; 130.67 (2C); 119.44; 114.79 (2C); 65.44; 55.31; 44.60; 38.00; 31.55; 27.98; 26.61; 21.31; 13.15.

Example 11

S-Butyl-2-(4-methoxyphenyl)-tetrahydrothiophenium triflate [1c(S-Bu)-CF$_3$SO$_3$]

CF$_3$SO$_3$H (98%, 2.25 g, 15 mmol) was added to a mixture of cyclic ether 7c (1.782 g, 10 mmol) and BuSH (0.902 g, 10 mmol). The reaction temperature was raised to 50° C. and the mixture was stirred for 24 h. H$_2$O (5 mL) and CH$_2$Cl$_2$ (10 mL) was added and the layers were separated. The aqueous-layer was extracted with CH$_2$Cl$_2$ (2×5 mL). The combined organic layers were washed with aqueous NaHCO$_3$ (sat., 5 mL), H$_2$O (5 mL) and dried (MgSO$_4$). Evaporation gave 3.80 g (95%) oil of 1c(S-Bu)-CF$_3$SO$_3$ as a 2/1 mixture of diastereomers. $^1$H-NMR: Major isomer 7.42 (d, 2H, Ar—H); 6.92 (d, 2H, Ar—H); 5.30 (dd, 1H, CHS); 4.05–3.50 (m, 7H, including CH$_2$S(ring), 2H, 3.81 (s, 3H, CH$_3$), and 3.57 (t, 2H, CH$_2$S)); 3.10–2.20 (m, 4H, CH$_2$(ring)); 1.76 (m, 2H, CH$_2$CH$_2$CH$_3$); 1.44 (m, 2H, CH$_2$CH$_3$); 0.90 (t, 3H, CH$_2$CH$_3$); Minor isomer (distinguishable peaks in mixture with major isomer) 7.48 (d, Ar—H); 6.96 (d, Ar—H); 5.53 (dd, CH$_2$S); 3.83 (s, CH$_3$O); 0.76 (t, 3H, CH$_2$CH$_3$). $^{13}$C-NMR: Major isomer 160.36; 129.27 (2C); 124.63; 123.71 (triflate); 114.72 (2C); 68.22; 55.16; 43.57; 42.86; 38.38; 28.40; 27.05; 21.17; 12.92; Minor isomer (distinguishable peaks in mixture with major isomer) 160.98; 130.56 (2C); 119.41; 117.34 (triflate); 114.72 (2C); 65.33; 52.21; 44.45; 37.81; 31.44; 27.83; 26.49; 21.17; 13.00.

Example 12

S-Butyl-2-(4-isopropylphenyl)-tetrahydrothiophenium hexafluorophosphate [1d(S-Bu)-PF$_6$]

Aqueous HPF$_6$ (60%, 2.92 g, 12 mmol) was added slowly to a solution of diol 6d (1.25 g, 6 mmol) and n-butylmercaptan (0.81 g, 9 mmol) in CH$_2$Cl$_2$ (8 mL). The reaction mixture was stirred for 24 h. Workup according to the general procedure A gave 1.42 g (58%) brown oil of 1d(S-Bu)-PF$_6$ as a 1.5/1 mixture of diastereomers. 100 mg of 1d(S-Bu)-PF$_6$ was washed with a H$_2$O$_2$-solution and to give a colorless oil. $^1$H-NMR: 7.50–7.13 (m, 4H, Ar—H); 5.40 (dd, 1H, CH—S, minor isomer); 5.16 (dd, 1H, CH—S, major isomer); 4.13–3.45 (m, CH$_2$—S); 3.06–2.20 (m, CH—CH$_2$—CH$_2$ and CH(CH$_3$)$_2$); 1.85–1.1 (m, CH$_2$—CH$_2$—CH$_3$); 1.24 (d, 6H, (CH$_3$)$_2$CH); 0.91 (t,3H, CH$_3$—CH$_2$, major isomer); 0.71 (t, 3H, CH$_3$—CH$_2$, minor isomer).

Example 13

S-Butyl-2-(4-tertbutylphenyl)-tetrahydro-thiophenium hexafluorophosphate [1e(S-Bu)-PF$_6$]

Aqueous HPF$_6$ (60%, 2.92 g, 12 mmol) was added slowly to a solution of diol 6e (1.33 g, 6 mmol) and BuSH (0.81 g, 9 mmol) in CH$_2$Cl$_2$ (8 mL) kept at 0° C. The reaction mixture was stirred for 24 h. Workup according to the general procedure A gave 1.28 g (51%) yellow oil of 1e(S-Bu)-PF$_6$ as a 2/1 mixture of diastereomers. $^1$H-NMR: 7.53–7.17 (m, 4H, Ar—H); 5.47 (dd, 1H, CH—S, minor isomer); 5.20 (dd, 1H, CH—S, major isomer); 4.16–3.46 (m, CH$_2$—S); 3.12–2.24 (m, CH—CH$_2$—CH$_2$); 2.02–0.8 (m, CH$_2$—CH$_2$—CH$_3$); 1.31.(s+s, 9H, (CH$_3$)$_3$C); 0.91 (t, 3H, CH$_3$—CH$_2$, major isomer); 0.70 (t, 3H, CH$_3$—CH$_2$, minor isomer).

Example 14

S-Butyl-2-(2,4-dimethylphenyl)-tetrahydrothiophenium hexafluorophosphate [1f(S-Bu)-PF$_6$]

The cyclic ether 7f (476 g, 2.7 mol) was reacted with BuSH (341 g, 3.78 mol) and aqueous HPF$_6$ (60%, 985 g, 4.05 mol) in CH$_2$Cl$_2$ (600 mL) and the reaction mixture was stirred for 17 h at RT. Workup according to the general procedure A gave 1.065 kg (100%) of crude 1f(S-Bu)-PF$_6$. Recrystallization in EtOH (920 mL) gave 745 (70%) white crystals of 1f(S-Bu)-PF$_6$ as a 1/1 mixture of diastereomers. $^1$H-NMR (aceton-d$_6$): 7.63 (d, 1H, Ar—H, major isomer); 7.49 (d, 1H, Ar—H, minor isomer); 7.27–7.13 (m, 2H, Ar—H); 5.65 (dd, 1H, J=12.5 and 5.0 Hz, CH—S, major isomer); 5.54 (dd, 1H, J=10.2 and 6.8 Hz, CH—S, minor isomer); 4.24–3.62 (m, CH$_2$—S); 3.20–2.25 (m, CH—CH$_2$—CH$_2$); 2.47 (s, 3H, Ar—CH$_3$, major isomer); 2.45 (s, 3H, Ar—CH$_3$, minor isomer); 2.35 (s, 3H, Ar—CH$_3$, major isomer); 2.31 (s, 3H, Ar—CH$_3$, minor isomer); 1.90 (m, CH$_2$); 1.6–0.8 (m, CH$_2$—CH$_2$—CH$_3$); 0.95 (t, 3H, C$_2$—CH$_3$, minor isomer); 0.74 (t, 3H, CH$_2$—CH$_3$, major isomer). $^{13}$C-NMR: 131.98; 128.00; 127.89; 127.52; 64.95; 62.46; 44.61; 43.55; 42.81; 38.50; 38.31; 31.40; 28.56; 27.34; 26.56; 21.25; 20.93; 19.34; 13.03. Anal. Calcd for C$_{16}$H$_{25}$SPF$_6$: C, 48.73; H, 6.39; S, 8.13. Found: C, 48.8; H, 6.5; S, 7.8

Example 15

S-tert-Butyl-2-(2,4-dimethylphenyl)-tetrahydrothiophenium hexafuorophosphate [1f(S-tert-Bu)-PF$_6$]

Aqueous HPF$_6$ (60%, 10.95 g, 45 mmol) was added to a mixture of diol 6f (5.82 g, 30 mmol) and t-BuSH (2.71 g, 30 mmol). After 2 hours' stirring, crystallization started. H$_2$O (15 mL) was added, the crystals were filtered and washed with H$_2$O (2×10 mL), aqueous NaHCO$_3$ (sat., 2×10 mL) and H$_2$O (10 mL). The crystals were dried to give 10.59 g (90%) white crystals of 1f(S-tBu)-PF$_6$ as a >30/1 mixture of two diastereomers. $^1$H-NMR: 7.36 (d, 1H, Ar—H); 7.06 (d, 1H, Ar—H), 7.02 (s, 1H, Ar—H); 5.06 (dd, 1H, CHS); 3.86–3.52 (m, 2H, CH$_2$S); 2.82–2.05 (m, 10H, including CH$_2$(ring), 4H, 2.42 (s, 3H, CH$_3$Ar), and 2.28 (s, 3H, CH$_3$Ar)); 1.54 (s, 9H, t-Bu). $^{13}$C-NMR: 137.79; 136.24; 135.65; 131.11; 126.98; 126.68; 48.49; 38.68; 33.19; 30.88; 20.97; 19.69.

Example 16

S-iso-Butyl-2-(2,4-dimethylphenyl)-tetrahydrothiophenium hexafuorophosphate [1f(S-iso-Bu)-PF$_6$]

Aqueous HPF$_6$ (60%, 10.95 g, 45 mmol) was added to a mixture of diol 6f (5.82 g, 30 mmol) and 1-BuSH (2.71 g, 30 mmol). The reaction mixture was stirred for 24 h. H$_2$O (10 mL) was added and crystallization started. The crystals were filtered and washed with H$_2$O (2×5 mL), aqueous NaHCO$_3$ (2×5 mL) and H$_2$O (5 mL). Drying gave 11.14 g (94%) of 1f(S-iso-Bu)-PF$_6$ as a 1.2/1 mixture of diastereomers. $^1$H-NMR: Major isomer 7.39 (d, 1H, Ar—H); 7.10 (s, 1H, Ar—H); 7.07 (d, 1H, Ar—H); 5.34 (dd, 1H, CHS); 4.12–3.35 (m, 4H, including CH$_2$(ring), 2H, and 3.38 (d, 2H, CHCH$_2$ )); 2.96–2.54 (m, 4H, CH$_2$(ring)); 2.43 (s, 3H, CH$_3$Ar); 2.34 (s, 3H, CH$_3$Ar); 1.33 (m, 1H, CH$_3$CH); 0.92 (d, 3H, CH$_3$CH); 0.78 (d, 3H, CH$_3$CH); Minor isomer (distinguishable peaks in mixture with major isomer) 7.25 (d, Ar—H); 5.22 (dd, CHS); 2.39 (s, CH$_3$Ar); 2.30 (s, CH$_3$Ar); 2.06 (m, CH$_3$CH); 1.08 (d, CH$_3$CH); 1.01 (d, CH$_3$CH). $^{13}$C-NMR: Major isomer 141.00; 137.96; 132.27; 128.18; 127.73; 123.12; 63.04; 46.98; 45.31; 31.63; 27.41; 26.42; 25.52; 21.11; 21.04 (2C); Minor isomer (distinguishable peaks in mixture with major isomer) 139.56; 135.93; 132.18; 128.45; 128.09; 127.47; 66.17; 51.76; 44.02; 38.57; 28.74; (25.52); 21.39; 20.91; 19.31 (2C).

Example 17

S-iso-Propyl-2-(2,4-dimethylphenyl)tetrahydrothiophenium hexafluorophosphate [1f(S-iso-Pr)-PF$_6$]

Aqueous HPF$_6$ (60%, 10.95 g, 45 mmol) was added to a mixture of diol 6f (5.82 g, 30 mmol) and i-PrSH (2.28 g, 30 mmol). The reaction mixture was stirred for 24 h. H$_2$O (10 mL) and CH$_2$Cl$_2$ (50 mL) was added and the layers were separated. The aqueous-layer was extracted with CH$_2$Cl$_2$ (2×10 mL). The combined organic layers were washed with aqueous NaHCO$_3$ (sat., 2×10 mL) and dried (MgSO$_4$). Evaporation gave 9.92 g (87%) of 1f(S-iso-Pr)-PF$_6$ as a 6/1 mixture of diastereomers. $^1$H-NMR: Major isomer 7.26 (d, 1H, Ar—H); 7.07 (d, 1H, Ar—H); 7.04 (s, 1H, Ar—H); 5.25 (dd, 1H, CHS(ring)); 4.06–3.57 (m, 3H, CH$_2$S and CH$_3$CH); 2.93–2.14 (m, 10 H, including CH$_2$(ring), 4H, 2.42 (s, 3H, CH$_3$Ar), and 2.30 (s, 3H, CH$_3$Ar)); Minor isomer (distinguishable peaks in mixture with major isomer) 7.50 (d, Ar—H); 5.36 (dd, CHS(ring)); 3.35 (m, CH$_3$CH); 2.45 (s, CH$_3$Ar); 0.56 (d, CH$_3$CH). $^{13}$C-NMR: Major isomer 139.45; 135.54; 132.21; 128.58; 128.14; 127.97; 64.37; 48.76; 41.29; 38.89; 28.66; 20.85; 19.69; 19.20; 18.76; Minor isomer (distinguishable peaks in mixture with major isomer) 141.05; 138.24; 123.55; 64.09; 44.11; 41.65; 32.21; 27.00; 19.32; 19.02; 18.92.

Example 18

S-Dodecyl-2-(2,4-dimethylphenyl)-tetrahydro-thiophenium hexafuorophosphate [1f(S-dodecyl)-PF$_6$]

Aqueous HPF$_6$ (60%, 7.30 g, 30 mmol) was added to a mixture of diol 6f (3.89 g, 20 mmol) and n-dodecylmercaptan (4.05 g, 20 mmol). The reaction mixture was stirred for 24 h. H$_2$O (10 mL) was added and the layers were separated. The aqueous-layer was extracted with CH$_2$Cl$_2$ (2×10 mL), the combined organic layers were washed with H$_2$O (5 mL) and aqueous NaHCO$_3$ (sat., 5 mL) and dried (MgSO$_4$). Evaporation and extractions with petroleumether gave 7.38 g (73%) colorless oil of 1f(S-dodecyl)-PF$_6$ as a 1.6/1 mixture of diastereomers. $^1$H-NMR: Major isomer 7.39 (d, 1H, Ar—H); 7.10 (s, 1H, Ar—H); 7.07 (d, 1H, Ar—H); 5.34 (dd, 1H, CHS(ring)); 4.09–3.40 (m, 4H, CH$_2$S); 2.90–2.20 (m, 10H, including CH$_2$(ring), 4H, 2.44 (s, 3H, CH$_3$Ar), and 2.34 (s, 3H, CH$_3$Ar)); 1.45–1.00 (m, 18H, CH$_2$); 0.87 (d, 3H, CH$_3$CH$_2$); Minor isomer (distinguishable peaks in mixture with major isomer) 7.24 (d, Ar—H); 5.20 (dd, C HS(ring)); 2.41 (s, CH$_3$Ar); 2.31 (s, CH$_3$Ar). $^{13}$C-NMR: 140.72; 139.38; 137.90; 135.72; 132.01; 128.29; 127.95; 127.82; 127.60; 127.46; 122.99; 65.49; 62.62; 44.60; 43.39; 38.92; 38.34; 31.65; 31.29; 29.33; 29.17; 29.08; 28.85; 28.79; 28.62; 28.48; 27.83; 27.21; 25.29; 24.61; 22.43; 20.85; 20.74; 19.20; 13.85.

Example 19

S-Phenyl-2-(2,4-dimethylphenyl)-tetrahydro-thiophenium hexafuorophosphate [1f(S-Ph)-PF$_6$]

Aqueous HPF$_6$ (60%, 10.95 g, 45 mmol) was added to a mixture of diol 6f (5.82 g, 30 mmol) and thiophenol (3.31 g, 30 mmol). The reaction mixture was stirred for 100 h. H$_2$O (15 mL) was added and the layer was decanted and extracted with CH$_2$Cl$_2$ (2×3 mL). The combined organic layers were dissolved in CH$_2$Cl$_2$ (80 mL), washed with aqueous NaHCO$_3$ (sat., 2×10 mL) and dried (MgSO$_4$). Evaporation gave 10.88 g (88%) of 1f(S-Ph)-PF$_6$ as a 2/1 mixture of diastereomers. $^1$H-NMR (CDCl$_3$+DMSO-D$_6$); Major isomer 7.90–6.43 (m, 8H, Ar—H); 5.69 (dd, 1H, ArCHS); 4.47–3.93 (m, 2H, CH$_2$S); 3.11–2.46 (m, 7H, including C H$_2$(ring), 4H, and 2.52 (s, 3H, CH$_3$Ar)); 2.20 (s, 3H, C H$_3$Ar); Minor isomer (distinguishable peaks in mixture with major isomer) 5.56 (dd, ArCHS); 2.31 (s, CH$_3$Ar); 1.98 (s, CH$_3$Ar).

Example 20

S-Butyl-2-(2,4-dimethylphenyl)-tetrahydro-thiophenium hexafluoroantimonate [1f(S-Bu)-SbF$_6$]

HSbF$_6$·H$_2$O (535 g, 1.545 mol) was added to a mixture of diol 6f (200 g, 1.03 mol) and BuSH (111 mL, 1.03 mol) kept at 20°–25° C. The reaction temperature was raised to 50° C. and the mixture was stirred for 24 h. H$_2$O (150 mL) was added and the aqueous-layer decanted. CH$_2$Cl$_2$ (500 mL) was added to the organic layer, washed with H$_2$O (400 mL), aqueous NaHCO$_3$ (200 mL) and dried (MgSO$_4$). Evaporation gave 346.8 g (69%) of 1f (S-Bu)-SbF$_6$ as a 1/1 mixture of diastereomers. Recrystallisation in EtOH (1 L) gave 256.5 g (51%) white crystals of 1f(S-Bu)-SbF$_6$ as a 4/1 mixture of diastereomers. Mp: 99.1°–101° C. $^1$H-NMR: Major isomer 7.39 (d, 1H, J=8.5 Hz, Ar—H); 7.12 (s, 2H, Ar—H); 5.31 (dd, 1H, J=12.2 and 4.8 Hz, SCH); 4.05–3.94 (m, 1H, SC H$_2$CH$_2$CH$_2$CH$_3$); 3.50–3.32 (m, 1H, SCH$_2$); 2.89–2.59 (m, 4H, CH$_2$); 2.43 (s, 3H, Ar—CH$_3$); 2.34 (s, 3H, Ar—C H$_3$); 1.50–1.10 (m, 4H, CH$_2$); 1.01–0.82 (m, 4H, CH$_2$); 0.73 (t, 3H, J=7 Hz, CH$_3$); Minor isomer (distinguishable peaks in mixture with major isomer) 7.24 (d, 1H, J=7.3 Hz, Ar— H); 7.15 (s, 2H, Ar—H); 5.18 (dd, 1H, J=10.3 and 6.5 Hz, SCH); 3.90–3.72 (m, 1H, SCH$_2$); 240 (s, 3H, Ar—H$_3$); 2.31 (s, 3H, Ar—H$_3$). $^{13}$C-NMR: Major isomer 141.11; 137.96; 132.27; 127.98; 127.84; 122.86; 63.09; 44.73; 38.92; 31.49; 27.59; 26.61; 21.41; 21.34; 19.33; 13.16; Minor isomer (distinguishable peaks in mixture with major isomer) 139.75; 135.89; 128.24; 128.18; 127.54; 65.89; 43.53; 43.28; 38.36; 28.79; 27.37; 21.41; 20.42; 13.16. IR: 1615; 1466; 1451; 820; 658 cm$^{-1}$. Anal. Calcd for C$_{16}$H$_{25}$SSbF$_6$: C, 39.61; H, 5.19; S, 6.61. Found: C, 39.3; H, 5.2; S, 6.6.

Example 21

S-Butyl-2-(2-methyl,4-methoxyphenyl)tetrahydrothiophenium hexafuorophosphate [1g(S-Bu)-PF$_6$]

Aqueous HPF$_6$ (60%, 5.8 mL, 39 mmol) was added to a mixture of diol 6g (5.54 g, 26 mmol) and BuSH (3.9 mL, 36.4 mmol) kept at 0° C. and under N$_2$-atmosphere. The temperature was raised to RT and the mixture was stirred for 17 h. H$_2$O (10 mL) and CH$_2$Cl$_2$ (10 mL) was added, the layers were separated and the aqueous-layer was extracted with CH$_2$Cl$_2$ (2×20 mL). The combined organic layers were washed with H$_2$O (10 mL), aqueous NaHCO$_3$ (sat., 10 mL) and dried (MgSO$_4$). Evaporation gave 9.309 g (76%) of 1g(S-Bu)-PF$_6$ as a 1/1 mixture of diastereomers. Recrystallization in EtOH (45 mL) gave 4.43 g (42%) of 1g(S-Bu)-PF$_6$ as white crystals. $^1$H-NMR: Major isomer 7.47 (s, 1H, Ar); 7.42 (s, 1H, Ar); 6.85–6.76 (m, 1H, Ar); 5.39–5.29 (m, 1H, Ar—CH), 4.08–3.91 (m, 2H, CH$_2$); 3.82 (s, 3H, OC H$_3$); 3.5–3.4 (m, 2H, CH$_2$); 2.09–2.62 (m, 2H, CH$_2$); 2.44 (s, 3H, CH$_3$); 1.80–1.20 (m, 6H, CH$_2$); 0.74 (t, 3H, J=7 Hz, C H$_3$); Minor isomer (distinguishable peaks in mixture with major isomer) 7.30 (s, 1H, Ar); 7.27 (s, 1H, Ar); 5.25–5.15 (m, 1H, Ar—CH); 3.80 (s, 3H, OCH$_3$); 2.42 (s, 3H, C H$_3$); 2.42 (2, 3H, CH$_3$); 0.91 (t, 3H, J=7 Hz, CH$_3$).

Example 22

S-Butyl-2-(2,4-dimethoxyphenyl)-tetrahydrothiophenium hexafuorophosphate [1 h(S-Bu)-PF$_6$]

Aqueous HPF$_6$ (60%, 3.9 mL, 26.52 mmol) was added to a mixture of diol 6 h (4 g, 17.68 mmol) and BuSH (2.7 mL, 24.75 mmol) kept at 0° C. and under N$_2$-atmosphere. The mixture turn red under the addition of HPF$_6$. The temperature was raised to RT and the reaction mixture was stirred for 16 h. H$_2$O (30 mL) and CH$_2$Cl$_2$ (50 mL) was added, the layers were separated and the aqueous-layer was extracted with CH$_2$Cl$_2$ (2×25 mL). The combined organic layers were was washed with H$_2$O (30 mL), aqueous NaHCO$_3$ (sat., 2×25 mL) and dried (MgSO$_4$). Evaporation gave 4.96 g (66%) yellow oil of 1 h(S-Bu)-PF$_6$ as a 3.7/1 mixture of diastereomers. $^1$H-NMR: Major isomer 7.4–7.15 (Ar—H); 6.55–6.45 (Ar—H); 5.02–4.92 (dd, 1H, CH—S); 3.90 (s, 3H, OCH$_3$); 3.79 (s, 3H, OCH$_3$); 3.65–3.55 (m, 2H, C H$_2$); 3.30 (t, 2H, S—CH$_2$CH$_2$CH$_2$CH$_3$); 2.80–2.40 (m, 4H, CH$_2$); 1.85–1.65 (m, 4H, CH$_2$); 0.94 (t, 3H, J=7.3 Hz, C H$_3$); Minor isomer (distinguishable peaks in mixture with major isomer) 5.29–5.18 (dd, 1H, CH—S); 4.05–3.95 (t, 2H, S—CH$_2$ CH$_2$CH$_2$CH$_3$); 0.66 (t, 3H, J=7.3 Hz, CH$_3$).

Example 23

S-Butyl-2-(2,4,6-trimethylphenyl)-tetrahydro-thiophenium hexafuorophosphate [1i(S-Bu)-PF$_6$]

Aqueous HPF$_6$ (60%, 2.92 g, 12 mmol) was added slowly to a solution of diol 6i (1.25 g, 6 mmol) and BuSH (0.81 g, 9 mmol) in CH$_2$Cl$_2$ (8 mL) kept at 0° C. The reaction mixture was stirred for 24 h. Workup according to general procedure A gave 1.46 g (59%) uellow oil of 1i(S-Bu)-PF$_6$ as a >10/1 mixture of diastereomers. $^1$H-NMR: 6.91 (s, 2H, Ar—H); 5.44 (dd, 1H, CH—S); 3.98–3.35 (m, 4H, C H$_2$—S); 2.9–2.2 (m, 4H, CH—CH$_2$CH$_2$); 2.43 (s, 6H, o-C H$_3$); 2.28 (s, 3H, p-CH$_3$); 1.73 (m, 2H, C H$_2$—CH$_2$—CH$_3$); 1.46 (sext, 2H, CH$_2$—CH$_3$); 0.91 (t, 3H, CH$_2$CH$_3$).

Example 24

S-Butyl-2-(2,6-dimethyl,4-methoxyphenyl)tetrahydrothiophenium hexafuorophosphate [1j(S-Bu)-PF$_6$]

Aqueous HPF$_6$ (60%, 4.9 mL, 33.44 mmol) was added to a mixture of diol 6j (5 g, 22.29 mmol) and BuSH (3.4 mL, 31.21 mmol) in CH$_2$Cl$_2$ (5 mL) kept at 0°C. and under N$_2$-atmosphere. The reaction mixture was stirred for 1 h 45 min at 0° C. and for 3 h at RT. H$_2$O (5 mL) was added and the layers were separated. The aqueous-layer was extracted with CH$_2$Cl$_2$ (2×5 mL). The combined organic layers were washed with H$_2$O (5 mL), aqueous NaHCO$_3$ (sat., 2×5 mL) and dried (MgSO$_4$). Evaporation gave 9.24 g (98%) of 1j(S-Bu)-PF$_6$. Recrystallization in EtOH gave 4.11 g (43%) white crystals of 1j(S-Bu)-PF$_6$ as a >10/1 mixture of diastereomers. 1H-NMR: 6.69 (s, 1H, Ar); 6.64 (s, 1H, Ar); 5.09–5.01 (m, 1H, Ar—CH); 3.89 (s, 3H, OCH$_3$); 3.65–3.61 (m, 2H, CH$_2$); 3.28–3.19 (m, 2H, CH$_2$); 2.73–2.65 (m, 2H, CH$_2$); 2.39 (s, 3H, Ar—CH$_3$); 2.32 (s, 3H, Ar—CH$_3$); 1.80–1.65 (m, 2H, CH$_2$); 1.55–1.40 (m, 2H, CH$_2$); 0.92 (t, 3H, J=7.2 Hz, CH$_3$). $^{13}$C-NMR: 140.9: 138.0; 132.2; 128.0; 127.8; 123.1; 62.8; 44.6; 38.7; 31.4; 27.4; 26.5; 21.3; 21.0; 19.3; 13.0.

Example 25

S-Butyl-2-(4-methoxyphenyl)-pyranium hexafluorophosphate [1k(S-Bu)-PF$_6$]

Aqueous HPF$_6$(60%, 2.92 g, 12 mmol) was added slowly to a solution of diol 6k (0.63 g, 3 mmol) and BuSH (0.14 g, 4.5 mmol) in CH$_2$Cl$_2$ (3 mL) kept at 0° C. The reaction mixture was stirred for 120 h. Workup according to the general procedure A gave 0.38 g (32%) brown oil of 1k (S-Bu)-PF$_6$ as a >10/1 mixture of diastereomers. $^1$H-NMR: 7.43 (d, 2H, Ar—H); 6.95 (d, 2H, Ar—H); 5.45 (brd, 1H, C H—S); 4.00–2.96 (m, 4H, CH$_2$—S); 3.83 (s, 3H, C H$_3$—O); 2.6–0.9 (m, 10H, CH$_2$); 0.80 (t, 3H, CH$_3$—CH$_2$).

Example 26

S-Butyl-[3,4]-benzo-2,5-dihydrothiophenium hexafluorophosphate (3A)

Aqueous HPF$_6$ (60%, 3.8 mL, 25.97 mmol) was added to a mixture of diol 12A (1 g, 7.42 mmol) and BuSH (1.6 mL, 14.48 mmol) kept at 0° C. and under N$_2$-atmosphere. The temperature was raised to RT and the reaction mixture was stirred for 66 h. H$_2$O (10 mL) and CH$_2$Cl$_2$ (50 mL) was added and the layers were separated. The aqueous-layer was extracted with CH$_2$Cl$_2$ (20 mL). The combined organic layers were washed with aqueous NaHCO$_3$ (sat., 10 mL) and dried (MgSO$_4$). Evaporation gave 1.41 g (56%) of 3A. $^1$H-NMR 7.5–7.15 (m, 4H, Ar); 5.03 (d, 2H, J=17 Hz, C H$_2$S); 4.60 (d, 2H,J=17 Hz, CH$_2$S); 3.16 (t, 2H, J=7HZ, S—CH$_2$); 1.8–1.6 (m, 2H, SCH$_2$CH$_2$); 1.6–1.25 (m, 2H, SCH$_2$CH$_2$CH$_2$); 0.92 (t, 3H, J=7 Hz, S(CH$_2$)$_3$CH$_3$). $^{13}$C-NMR 133.18; 129.0; 125.93; 46.34; 39.94: 25.91; 21.44; 13.19 IR: 3632; 2962; 2876; 1826; 1585; 1490; 1459; 1409; 1286; 1246; 1212; 1055; 961; 916; 888; 753; 692; 521; 425.

Example 27

S-Butyl-2-phenyl-[3,4]-benzo-2,5-dihydro-thiophenium hexafluorophosphate (3B)

Aqueous HPF$_6$ (60%, 2.4 mL, 16.34 mmol) was added to a mixture of diol 12B (1 g, 4.67 mmol) and BuSH (1 mL, 9.3 mmol) kept at 0° C. and under N$_2$-atmosphere. After 30 minutes stirring, CH$_2$Cl$_2$ (1.5 mL) was added and the temperature was raised to RT. The reaction mixture was stirred for 7 h. H$_2$O (10 mL) and CH$_2$Cl$_2$ (50 mL) was added and the layers were separated. The aqueous-layer was extracted with CH$_2$Cl$_2$ (20 mL). The combined organic layers were washed with aqueous NaHCO$_3$ (sat., 15 mL) and dried (MgSO$_4$). Evaporation gave 1.385 g (69%) of 3B (containig 8% of 3A) as a 2.2/1 mixture of diastereomers. $^1$H-NMR d=7.6–7.2 (m, 18H, Ar—H, major+minor); 7.05 (s, 1H, Ar—CH—S, minor); 6.49 (s, 1H, Ar—CH—S, major); 5.1 (d, 1H, J=17 Hz, CH$_2$—S, minor); 5.0 (d, 2H, J=17 Hz, CH$_2$—S, major); 4.83 (d, 2H, J=17 Hz, C H$_2$—S, major); 4.74 (d, 2H, J=17 Hz, CH$_2$—S, minor); 3.65–3.5 (m, 1H, S—CH$_2$, major); 3.4–3.3 (m, 2H, S—C H$_2$, major); 2.95–2.8 (m, 1H S—CH$_2$, minor); 2.65–2.5 (m, 1H, S—CH$_2$, minor); 1.9–1.7 (m, 4H, SCH$_2$—CH$_2$, major+ minor); 1.5–1.3 (m, 4H, SCH$_2$CH$_2$—CH$_2$, major+minor); 0.91 (t, 3H, J=7 Hz. S(CH$_2$)$_3$CH$_3$, major); 0.68 (t, 3H, J=7 Hz, S(CH$_2$)$_3$CH$_3$, minor). IR: 2963; 2875; 2360; 1488; 1456; 1414; 1287; 1055; 753; 706; 601; 522; 430.

Example 28

S-Butyl-2-iso-propyl-[3,4]-benzo-2,5-dihydrothiophenium hexafluorophosphate (3C)

Aqueous HPF$_6$ (60%, 1.15 mL, 7.8 mmol) was added to a mixture of diol 12C (0.4 g, 2.23 mmol) and BuSH (0.5 mL, 4.46 mmol) kept at 0° C. and under N$_2$-atmosphere. The temperature was raised to RT and the reaction mixture was stirred for 6 h. H$_2$O (6 mL) and CH$_2$Cl$_2$ (30 mL) was added and the layers were separated. The aqueous-layer was extracted with CH$_2$Cl$_2$ (10 mL). The combined organic layers were washed with aqueous NaHCO$_3$ (sat., 10 mL) and dried (MgSO$_4$). Evaporation gave 0.37 g (38%) of 3C as a 3.3/1 mixture of diastereomers. $^1$H-NMR 7.53–7.4 (m, 8H, Ar, major+minor); 5.46 (d, 1H, J=7 Hz, (CH$_3$)$_2$CHCH, minor), 4.93 (s, 1H, (CH$_3$)$_2$CHCH, major); 4.90 (d, 1H, J=17 Hz, CH$_2$—S, minor); 4.90 (d, 1H, J=17 Hz, C H$_2$—S, major); 4.75 (d, 1H, J=17 Hz, CH$_2$—S, major); 4.58 (d, 1H, J=17 Hz, CH$_2$—S, minor); 3.45–3.1, 3–2.85, 2.7–2.45 (m, 6H, SCH$_2$, major+minor samt (CH$_3$)$_2$CH, major+minor); 1.88–1.73 (m, 4H, SCH$_2$CH$_2$, major+minor); 1.61–1.46 (m, 4H, SCH$_2$CH$_2$CH$_2$, major+minor); 1.35 (d, 3H,J=7 Hz, CH$_3$, minor); 1.33 (d, 3H,J=7 Hz, CH$_3$, minor); 1.26 (d, 3H,J=7 Hz, CH$_3$, major); 0.98 (d, 3H, J=7 Hz, C H$_3$, major); 0.97 (t, 3H, J=7 Hz, S(CH$_2$)$_3$CH$_3$, major); 0.93 (t, 3H, J=7 Hz, S(CH$_2$)$_3$CH$_3$, minor). $^{13}$C-NMR 130; 129.5; 126.1; 73.2; 46.2; 41.3; 33.8; 26.3; 21.5; 20.7; 18.1; 13.3. IR: 3636; 2965; 2877; 1631; 1468; 1417; 1394; 1374; 1286; 1056; 759; 522; 440.

Example 29

S-Butyl-2,2-dimethyl-[3,4]-benzo-2,5-dihydrothiophenium hexafluorophosphate (3D)

Aqueous HPF$_6$ (60%, 3 mL, 21 mmol) was added to a mixture of diol 12D (1 g, 6 mmol) and BuSH (1.3 mL, 12 mmol) kept at 0° C. and under N$_2$-atmosphere. The reaction mixture was stirred for 1 hour at 0° C. and for 49 h at RT. H$_2$O (10 mL) and CH$_2$Cl$_2$ (10 mL) was added and the layers were separated. The aqueous-layer was extracted with CH$_2$Cl$_2$ (3×10 mL). The combined organic layers were washed with aqueous NaHCO$_3$ (sat., 10 mL) and dried (MgSO$_4$). Evaporation and extractions with petroleumether gave 1.1 g (43%) of 3D as yellow crystals. $^1$H-NMR 7.55–7.4 and 7.3–7.05 (m, 4H, Ar—H); 5.04 (d, 1H, J=16 Hz, CH$_2$—S); 4.7 (d, 1H, J=17 Hz, CH$_2$—S); 3.42–3.25 (m, 1H, S—CH$_2$); 3.08–2.9 (m, 1H, S—CH$_2$); 2.03 (s, 3H, CH$_3$); 1.88 (m, 3H, CH$_3$); 1.9–1.7 (m, 2H, SCH$_2$—CH$_2$); 1.6–1.4 (m, 2H, SCH$_2$CH$_2$CH$_2$); 0.94 (t, 3H, J=7 Hz, S(CH$_2$)$_3$CH$_3$). $^{13}$HC-NMR 142.4; 132.2; 129,9; 126.6; 123.1; 71.6; 42.3; 36.9; 29.3; 26.6; 22.4; 21.8; 13.3. IR: 2971; 2878; 1485; 1468; 1456; 1410; 1376; 1103; 838; 766; 735; 558; 437.

Example 30

S-Butyl-2-metyl-2-phenyl-[3,4]-benzo-2,5-dihydrothiophenium hexafluorophosphate (3E)

Aqueous HPF$_6$ (60%, 3 mL, 21 mmol) was added to a mixture of diol 12E (600 mg, 2.63 mmol) and BuSH (1.3 mL, 12 mmol) kept at 0° C. and under N$_2$-atmosphere. The temperature was raised to RT and the reaction mixture was stirred for 4.5 h. H$_2$O (10 mL) and CH$_2$Cl$_2$ (10 mL) was added and the layers were separated. The aqueous-layer was extracted with CH$_2$Cl$_2$ (3×10 mL). The combined organic layers were washed with aqueous NaHCO$_3$ (sat., 10 mL) and dried (MgSO$_4$). Evaporation gave 1.135 g (73%) of 3E, $^1$H-NMR 7.55–7.4 and 7.3–7.05 (m, 4H, Ar—H); 5.04 8d, 1H J=16 Hz, CH$_2$—S); 4.7 (d, 1H, J=17 Hz, CH$_2$—S); 3.42–3.25 (m, 1H, S—CH$_2$); 3.08–2.9 (m, 1H, S-CH$_2$); 2.03(s, 3H, CH$_3$); 1.88 (s, 3H, CH$_3$); 1.9–1.7 (m, 2H, S—CH$_2$—CH$_2$); 1.6–1.4 (m, 2H, S—CH$_2$—CH$_2$); 0.94 (t, 3H, J=7 Hz, S—(CH$_2$)$_3$CH$_3$). $^{13}$C-NMR 139.7; 137.5; 134.5; 130.6; 130.1; 129.5; 127.64; 127.4; 125.6; 78.3; 41.4; 37.1; 26.5; 22.9; 21.9; 13.4. IR: 2946; 2878; 1493; 1456; 1407; 1392; 1289; 1215; 1191; 1061; 782; 762; 737; 703; 650; 613; 561; 522.

Example 31

S-Butyl-2,2-diphenyl-[3,4]-benzo-2,5-dihydrothiophenium hexafluorophosphate (3F)

Aqueous HPF$_6$ (60%, 1.8 mL, 12 mmol) was added to a mixture of diol 12F (1 g, 3.44 mmol) and BuSH (0.74 mL, 6.9 mmol) kept at 0° C. and under N$_2$-atmosphere. After 1 hours stirring at 0° C., CH$_2$Cl$_2$ (0.5 mL) was added and the reaction mixture was stirred for 21 h at RT. H$_2$O (6 mL) and CH$_2$Cl$_2$ (30 mL) was added and the layers were separated. The aqueous-layer was extracted with CH$_2$Cl$_2$ (10 mL). The combined organic layers were washed with aqueous NaHCO$_3$ (sat., 6 mL) and dried (MgSO$_4$). Evaporation gave 1.208 g (60%) of 3F. $^1$H-NMR 7.6–7.35 (m, 14H, Ar—H); 5.02 (s, 2H, CH$_2$—S); 3.25–3.1 (m, 1H, S—CH$_2$); 2.7–2.5 (m, 1H, S—CH$_2$); 1.6–1.35 (m, 2H, SCH$_2$CH$_2$); 1.35–1.1 (m, 2H, SCH$_2$CH$_2$CH$_2$); 0.7 (t, 3H, J=7 Hz, S(CH$_2$)$_3$CH$_3$). $^{13}$C-NMR 131.1; 130.5; 1.35; 130.3; 129.6; 129.4; 127.4; 127.6; 127.2; 45.8; 40.1; 26.3; 21.67; 13.0. IR=3436; 2964; 1495; 1451; 1410; 1285; 1241; 1056; 769; 757; 744; 698; 634; 623; 521; 437.

Example 32

S-Butyl-5-methyl-[3,4]-benzo-2,7-dihydrothiephinium hexafluorophosphate (5A)

The diol 12G (50 mg, 0.281 mmol) was added to a mixture of aqueous HPF$_6$ (60%, 144 μL, 0.98 mmol), BuSH (60 μL, 0.56 mmol) and CH$_2$Cl$_2$ (500 μL) kept at 0° C. The reaction mixture was stirred for 6 h at RT. H$_2$O and CH$_2$Cl$_2$ was added and the layers were separated. The aqueous-layer was extracted with CH$_2$Cl$_2$ and the combined organic layers were washed with aqueous NaHCO$_3$ (sat.) and dried (MgSO$_4$). Evaporation and extractions with petroleumether gave 50 mg (47%) of 5A. $^1$H-NMR 7.6–7.3 (m, 4H Ar—H); 6.1 (t, 1H, C═CH) 4.45 (d, 1H, J=13 Hz, ArCH$_2$S); 4.16 (d, 1H, J=13 Hz, ArCH$_2$S); 3.75–3.62 (m, 1H, SCH$_2$); 3.45–3.15 (m, 3H, SCH$_2$+C═CHCH$_2$S); 1.88–1.72 (m, 2H, SCH$_2$CH$_2$); 1.6–1.4 (m, 2H, SCH$_2$CH$_2$CH$_2$); 0.95 (t, 3H, J=7 Hz, S(CH$_2$)$_3$CH$_3$). $^{13}$C-NMR 148.5; 141.1; 131.5; 130.7; 129.1; 127.8; 125.6; 114.7; 39.2; 38.7; 35.2; 25.9; 23; 21.6; 13.1. IR: 3629; 2963; 2875; 1636; 1490; 1424; 1285; 1056; 769; 521.

Example 33

S-Butyl-5-phenyl-[3,4]-benzo-2,7-dihydrothiephinium hexafluorophosphate (5B)

Aqueous HPF$_6$ (60%, 2.4 mL, 16.34 mmol) was added to a mixture of diol 12I (1 g, 4.67 mmol) and BuSH (1 mL, 9.3 mmol) kept at 0° C. and under N$_2$-atmosphere. After 30 minutes stirring at RT CH$_2$Cl$_2$ (1.5 mL) was added. The reaction mixture was stirred for 6 more h. H$_2$O (10 mL) and CH$_2$Cl$_2$ (50 mL) was added and the layers were separated. The aqueous-layer was extracted with CH$_2$Cl$_2$ (20 mL). The combined organic layers were washed with aqueous NaHCO$_3$ (sat., 15 mL) and dried (MgSO$_4$). Evaporation gave 1.385 g (60%) of 5B. $^1$H-NMR 7.65–7.15 (m, 9H, Ar—H); 6.52-(t, 1H, J=7 Hz, C═CH); 4.54 (d, 1H, J=14 Hz, ArCH$_2$S); 4.21 (d, 1H, J=14 Hz, ArCH$_2$S); 3.48–3.18 (m, 3H, SCH$_2$ and C═CHCH$_2$S); 1.92–1.73 (m, 2H, SCH$_2$CH$_2$); 1.63–1.41 (m, 2H, SCH$_2$CH$_2$CH$_2$); 0.96 (t, 3H, J=7 Hz, S(CH$_2$)$_3$CH$_3$). $^{13}$C-NMR 151.3; 139.6; 138.5; 131.7; 131; 129.9; 129.6; 128.7; 128.2; 127.4; 114.7; 39.6; 39.2; 21.8; 13.3. IR: 3414; 2961; 1617; 1447; 1059; 766; 700; 634; 522.

Example 34

S-Butyl-isothiochromanium hexafluorophosphate [4a(S-Bu)-PF$_6$]

Aqueous HPF$_6$ (60%, 7.30 g, 30 mmol) was added slowly to a mixture of isochromanone (13) (2.68 g, 20 mmol) and BuSH (1.80 g, 20 mmol). The reaction mixture was stirred for 1 week at RT and for 2 days at 50° C. H$_2$O (10 mL) was added and the layers were separated. The aqueous-layer was extracted with CH$_2$Cl$_2$ (2×20 mL). The combined organic layers were washed with aqueous NaHCO$_3$ (sat., 2×10 mL) and dried (MgSO$_4$). Evaporation gave 5.95 g (85%) of 4a(S-Bu)-PF$_6$. $^1$H-NMR: 7.53–7.10 (m, 4H, Ar—H); 4.44 (dd, 2H, ArCH$_2$S); 4.08–2.80 (m, 6H, CH$_2$); 1.73 (m, 2H, CH$_2$CH$_2$S); 1.46 (m, 2H, CH$_2$CH$_3$); 0.92 (t, 3H, CH$_3$). $^{13}$C-NMR (DMSO-D$_6$): 135.64; 129.57; 129.34; 128.97; 127.62; 126.55; 39.57; 35.65; 35.31; 25.27; 25.10; 20.96; 13.14.

Example 35

S-Benzyltetrahydrothiophenium hexafluorophosphate (2)

Aqueous HPF$_6$ (60%, 13.99 g, 57.5 mmol) was added to a mixture of THF (2.07 g, 28.55 mmol) and benzylmercaptan (5 g, 28 mmol). The reaction mixture was stirred for 21 h. H$_2$O (13 mL) and CH$_2$Cl$_2$ (13 mL) was added and the layers were separated. The aqueous-layer was extracted with CH$_2$Cl$_2$ (2×20 mL). The combined organic layers were washed with H$_2$O (20 mL), aqueous NaHCO$_3$ (sat., 2×20 mL) and dried (MgSO$_4$). Evaporation gave 3.633 (40%) of 2. $^1$H-NMR (aceton-d$_6$): 7.67–7.63 (m, 2H, Ar—H$_2$); 7.52–7.50 (m, 3H, Ar—H); 4.76 (s, 2H, ArCH$_2$S); 3.75–3.66 (m, 2H, CH$_2$); 2.51–2.41 (m, 2H, CH$_2$). $^{13}$C-NMR (aceton-d$_6$): 131.31 (2C); 130.75; 130.46 (2C); 46.58; 43.55;

Example 36

Kinetic study of formation of S-Butyl-2-(2,4-dimethylphenyl)-tetrahydrothiophenium hexafluorophosphate [1f(S-Bu)-PF$_6$]

Aqueous HPF$_6$ (31%, 1.5 eq) was added to a mixture of diol 6f (1 eq) and BuSH (1 eq). The reaction mixture was stirred at 25° C. and monitored by $^1$H-NMR analysis. Samples of 0.2 mL were diluted with CDCl$_3$ (1 mL) and neutralized with K$_2$CO$_3$ followed by filtration through cotton. Cyclic ether 7f:$^1$H-NMR: 7.32 (d, 1H, Ar—H); 7.00 (d, 1H, Ar—H); 6.95 (s, 1H, Ar—H); 5.05 (t, 1H, J=7.0 Hz, CH—O); 4.13 (q, 1H, CH$_2$—O); 3.92 (q,1H, CH$_2$); 2.42–2.24 (m, 1H, CH$_2$); 2.30 (s, 1H, CH$_3$—Ar); 2.27 (s, 1H, CH$_3$—Ar); 1.99 (quint, 2H, CH$_2$CH); 1.76–1.57 (m, 1H, CH$_2$). Sulfido alcohol, 8f(S-Bu): $^1$H-NMR: 7.31 (d, 1H, Ar—H); 6.99 (d, 1H, Ar—H); 6.94 (s, 1H, Ar—H); 4.05 (t, 1H, J=7.5 Hz, CH—S); 3.58 (t, 2H, J=6.4 Hz, CH$_2$—O); 2.31 (s, 3H, CH$_3$—Ar); 2.28 (s, 3H, CH$_3$—Ar); 2.0–1.8 (m, 2H, CH$_2$); 1.7–1.2 (m, 4H, CH$_2$); 0.83 (t, 3H, CH$_3$).

Example 37

Transformation of the diol 6c to the cyclic ether 7c

To a ether solution (50 mL) of the diol 6c (2.94 g, 15 mmol) was added concentrated sulfuric acid (4 drops, 80 mg). The reaction mixture was stirred an 25° C. for 2 h. Saturated NaHCO$_3$ (aqueous 2 mL) was added and the organic phase was collected, dried and concentrated to yield 2.6 g (97%) of 7c as a colorless liquid. $^1$ H-NMR: 7.26 (d, 2H, J=8.6, Ar—H); 6.87 (d, 2H, J=8.7, Ar—H); 4.87 (t, 1H, J=7.0, CH—S); 4.20–3.89 (m, 2H, CH$_2$S), 3.84 (s, 3H, MeO), 2.40–1.77 (m, 4H, C—CH$_2$—CH$_2$—C).

Example 38

Synthesis of S,S'-ethylene-1,2-bis[2-(4-methoxyphenyl)tetrahydrothiophenium hexafluorophospate]1c(S,S'-ethylene)-PF$_6$ To a mixture of cyclic ether 7c (712 mg, 4 mmol) and 1,2-dimercaptoethane (188 mg, 2 mmol) was slowly added aqueous HPF6 (1.1 mL, 60% w/w, 8 mmol). After stirring for 1 h at 25° C. water (2 mL) was added and the slurry was filtrated. The crystals were washed with water and aqueous NaHCO$_3$ and dried yielding 1.40 g (99%) of 1c(S,S'-ethylene)-PF$_6$ as yellow crystals. mp=118°–122° C. $^1$H-NMR (acetone-d$_6$) 7.6–7.0 (m, 4H, Ar—H); 5.9–5.3 (m, 1H, CH—S); 4.4–3.7 (8H, including MeO); 3.0–2.4 (m, 4H). Anal. Calcd for C$_{24}$H$_{32}$S$_2$P$_2$F$_{12}$: C, 40.8; H, 4.56; S, 9.10; P, 8.7. Found: C, 40.3; H, 4.6; S, 9.2; P, 8.3.

Example 39

Synthesis of S,S'-hexylene-1,6-bis[2-(4-methoxyphenyl)tetrahydrothiophenium hexafluorophospate] [1c(S,S'-hexylene)-PF$_6$]HPF$_6$ (1.47 mL, 10 mmol) was added to a solution of THF-derivative 7c (890 mg, 5 mmol) and 1,6-dimercaptohexane (375 mg, 2.5 mmol). The reaction mixture was stirred for 2 h at 25° C. Water (3 mL) was added and the reaction mixture was extracted with CH$_2$Cl$_2$ (3×2 mL) and the combined organic layers were washed with aqueous NaHCO$_3$ (sat., 2×1 mL). Drying with MgSO$_4$ and evaporation gave the disalt as white crystals, 1.9 g (83%). mp=56°–62° C. $^1$H-NMR(aceton-d$_6$): 7.64–7.50 (m, 2H, Ar—H); 7.12–6.96 (m, 2H, Ar—H); 5.69–5.57 (m, 0.5 H, CH—S); 5.40–5.22 (m, 0.5H, CH—S); 4.18–3.48 (m, 14H, CH$_2$—S and); 3.90–3.48 (m, CH$_2$—S and OCH$_3$); 3.20–1.05 (m,16H, —CH$_2$—).

Example 40

Synthesis of S,S'-p-xylylene-bis[2-(4-methoxyphenyl)tetrahydrothiophenium hexafluorophospate][1c(S,S'-p-xylylene)-PF$_6$]

HPF$_6$ (0.5 mL, 3.5 mmol) was added to a solution of cyclic ether 7c (155 mg, 0.87 mmol) and p-xylene-α,α'-dithiol (74 mg, 0.43 mmol). The reaction mixture was stirred for 4 h at 25° C. Water (3 mL) was added and the slurry was filtrated. The crystals were washed with NaHCO$_3$ (aq) and dried to yield 280 mg (86%) of 1c(S,S'-p-xylylene)-PF$_6$ as yellow crystals. mp=96°–103° C.1H-NMR(acetone-d$_6$): 7.80–6.74 (m, 12H, Ar—H); 5.82–5.66 and 5.50–5.30 (m, 2H, CH—S); 5.07 and 5.01 (two s, benzylic); 4.59–3.52 (m, 10H, CH$_2$—S and CH$_3$O); 3.00–2.33 (m, 8H, CH$_2$—).

Example 41

Synthesis of 1c(S-Bu)-PF$_6$ by addition of diol/ether to acid/mercaptan-mixture Cyclic ether 7c (155 mg, 0.87 mmol) was added dropwise to a mixture of HPF$_6$ (0.25 mL, 1.74 mmol) and BuSH (79 mg, 0.87 mmol) and the reaction mixture was stirred for 4 h at 25° C. Workup according to the general procedure A yielded 254 mg (95%) of 1c(S-Bu)-PF$_6$ as white crystals. General procedure for the synthesis of ketoacids (11)

AlCl$_3$ (95%, 2 eq) was added to an ice-cooled slurry of succinic anhydride (99%, 1 eq) in the aromatic compound 10 (4.3–6 eq). The reaction mixture was stirred at RT for the indicated time and than cooled with ice. HCl (2M) was added in small portions. The resulting crude product was filtrated and dried. For most cases the crude product was used in the proceeding step. The acids was in some cases purified by the following procedure: the crystals were dissolved in NaOH (2M) and the solution was extracted with diethylether. The aqueous phase was acidified with HCl (conc.) to pH<1 and the acid pricipitates. The crystals were filtrated, washed with HCl (2M) and H$_2$O and dried to give 11.

3-(4-Methylbenzoyl)-propionic acid (11b)

Toluene 10b (99.9%, 5.5 eq) was reacted with succinic anhydride (99%, 1 eq) and AlCl$_3$ (95%, 2 eq) for 24 h according to the general procedure. Yellow crystals of 11b were obtained in 75% yield. $^1$H-NMR: 7.88 (d, 2H, J=8.2 Hz, Ar—H); 7.26 (d, 2H, J=4.8 Hz, Ar—H); 3.29 (t, 2H, J=6.6 Hz, CH$_2$CH$_2$COOH); 2.80 (t, 2H, J=6.6 Hz, CH$_2$CH$_2$COOH); 2.41 (s, 3H, CH$_3$). $^{13}$C-NMR: 192.44; 178.70; 144.13; 133.91; 129.29; 128.14; 33.02; 28.06; 21.63.

3-(4-Methoxybenzoyl)-propionic acid (11c)

Anisole 10c (4 L, 99%, 37 mol) was reacted with succinic anhydride (670 g, 99%, 6.7 mol) and AlCl$_3$(1.88 kg, 95%, 14.1 mol) for 20 h according to the general procedure. Fluid bed drying of the crude product afforded 1.0 kg (72%) yellowish crystals of 11c. $^1$H-NMR: 7.97 (d, 2H, J=8.9 Hz, Ar—H); 6.94 (d, 2H, J=8.9 Hz, Ar—H); 3.87 (s, 3H, OCH$_3$); 3.27 (t, 2H, J=6.7 Hz; CH$_2$CH$_2$COOH); $^{13}$C-NMR (CDCl$_3$+DMSO-d$_6$): 196.22; 174.29; 162.95; 129.68 (2C); 129.21; 113.19 (2C); 54.95; 32.67; 27.70. IR (KBr): 2973; 1702; 1655; 1598; 1486; 1439; 1289; 1260; 1246; 757 cm$^{-1}$.

3-(4-iso-Propylbenzoyl)-propionic acid (11d)

Cumene 10d (99%, 4.8eq) was reacted with succinic anhydride (99%, 1 eq) and AlCl$_3$ (95%, 2 eq) for 120 h according to the general procedure. Extractive purification of the crude product afforded white crystals of 11d were obtained in 83% yield. $^1$H-NMR: 7.92 (d, 2H, Ar—H); 7.32 (d, 2H, Ar—H); 3.30 (t, 2H, CH$_2$CH$_2$COOH); 2.97 (sept., 1H,CH(CH$_3$)$_2$); 2.81 (t, 2H, CH$_2$CH$_2$COOH); 1.27 (d, 6H, CH(CH$_3$)$_2$).

3-(4-tert-Butylbenzoyl)-propionic acid (11e)

tert-Butylbenzene 10e (99%, 4.3 eq) was reacted with succinic anhydride (99%, 1 eq) and AlCl$_3$ (95%, 2 eq) for 120 h according to the general procedure. Extractive purification of the crude product afforded white crystals of 11e in 68% yield. $^1$H-NMR: 7.93 (d, 2H Ar—H); 7.48 (d, 2H, Ar—H); 3.30 (t, 2H, CH$_2$CH$_2$COOH); 2.81 (t, 2H, CH$_2$CH$_2$COOH); 1.34 (s, 9H, CH$_3$).

3-(2,4-Dimethylbenzoyl)-propionic acid (11f)

m-Xylene 10f (98%, 5.5 eq) was reacted with succinic anhydride (99%, 1 eq) and AlCl$_3$ (95%, 2 eq) for 42 h according to the general procedure. Extractive purification of the crude product afforded white crystals of 11f were obtained in 92% yield. $^1$H-NMR: 7.66 (d, 1H, Ar—H); 7.07 (d, 2H, Ar—H); 3.22 (t, 2H, CH$_2$CH$_2$COOH); 2.77 (CH$_2$CH$_2$COOH); 2.49 (s, 3H, CH$_3$); 2.35 (s, 3H, CH$_3$).

3-(2-Methyl-4-methoxybenzoyl)-propionic acid (11g)

3-Methylanisole 10g (99%, 6 eq) was reacted with succinic anhydride (99%, 1 eq) and AlCl$_3$ (95%, 2 eq) for 20 h according to the general procedure. White crystals of 2 isomers were obtained: 3-(2-methyl-4-methoxybenzoyl)-propionic acid (53%) and 3-(2-methoxy-4-methylbenzoyl)-propionic acid (27%). The crude product was recrystallized in EtOH to give pure β-(2-methyl-4-methoxybenzoyl)-propionic acid (11g) in 24% yield. $^1$H-NMR: 7.80 (d, 1H, J=9.4 Hz; Ar—H); 6.79–6.75 (m, 2H, Ar—H); 3.85 (s, 3H, OCH$_3$); 3.24 (t, 2H, J=6.3 Hz, CH$_2$CH$_2$COOH); 2.77 (t, 2H, J=6.3 Hz, CH$_2$CH$_2$COOH); 2.25 (s, 3H, CH$_3$). $^{13}$C-NMR: 199.16; 178.33; 162.04; 142.35; 131.67; 117.54; 110.67; 110.62; 55.30; 35.02; 28.39; 22.47.

3-(2,4-Dimethoxybenzoyl)-propionic acid (11 h)

1,3-Dimethoxybenzene 10 h (99%, 6 eq) was reacted with succinic anhydride (99%, 1 eq) and AlCl$_3$ (95%, 2 eq) for 19 h according to the general procedure. Recrystallization in EtOH gave white crystals of 11 h in 68% yield. $^1$H-NMR: 7.89 (d, 1H, J=8.7 Hz, Ar—H; 6.55 (dd, 1H, J=8.7 and 2.3 Hz, Ar—H); 6.46 (d, 1H, J=2.3 Hz, Ar—H); 3.91 (s, 3H, OCH$_3$); 3.86 (s, 3H, OCH$_3$); 3.30 (t, 2H, J=6.6 Hz, CH$_2$CH$_2$COOH); 2.73(t, 2H, J=6.6 Hz, CH$_2$CH$_2$COOH). $^{13}$C-NMR: 197.62; 164.79; 161.23; 132.96; 105.29; 98.31; 55.54; 55.47; 38.42; 28.67.

3-(2,4,6-Trimethylbenzoyl)-propionic acid (11i)

Mesitylene 10i (99%, 4.8 eq) was reacted with succinic anhydride (99%, 1 eq) and AlCl$_3$ (95%, 2 eq) for 72 h according to the general procedure. Extractive purification of the crude product afforded white crystals of 11i in 54% yield. $^1$H-NMR (DMSO-d$_6$): 6.63 (s, 2H, Ar—H); 2.84 (t, 2H, CH$_2$CH$_2$COOH); 2.22 (s, 3H, p-CH$_3$); 2.18 (t, 2H, CH$_2$CH$_2$COOH); 2.13 (s, 6H, o-CH$_3$).

-(2,6-Dimethyl-4-methoxybenzoyl)-propionic acid (11j)

3,5-Dimethylanisol 10j (99%, 6 eq) was reacted with succinic anhydride (99%, 1 eq) and AlCl$_3$ (95%, 2 eq) for 20 h according to the general procedure. Extractive purification of the crude product afforded white crystals of 11j in 93% yield. $^1$H-NMR: 6.63 (s, 1H, Ar—H); 6.56 (s, 1H, Ar—H); 3.79 (s, 3H, OCH$_3$); 3.11 (t, 2H, J=6.7 Hz, CH$_2$CH$_2$COOH); 2.75 (t, 2H, J=6.7 Hz, CH$_2$CH$_2$COOH); 2.32 (s, 3H, CH$_3$); 2.19 (s,, 3H, CH$_3$). $^{13}$C-NMR: 205.32; 178.97; 156.41; 140.41; 136.05; 127.36; 123.73; 109.01; 55.41; 38.84; 28.04; 21.49; 18.85.

3-(4-Methoxybenzoyl)-butanoic acid (11k)

Anisole 10k (99%, 6.1 eq) was reacted with glutaric anhydride (98%, 1 eq) and AlCl$_3$ (95%, 2 eq) for 120 h according to the general procedure. Extractive purification of the crude product afforded 66% of 11k as a black oil. $^1$H-NMR (Aceton-d$_6$): 7.99 (d, 2H, Ar—H); 7.02 (d, 2H, Ar—H); 3.89 (s, 3H, CH$_3$); 3.06 (t, 2H, CH$_2$CO); 2.42 (t, 2H, CH$_2$COOH); 1.97 (quint, 2H, CH$_2$COOH).

General procedure for the synthesis of 1-Aryl-1,4-butandiols (6)

The ketoacid, 11 (1 eq, as crystals or dissolved in THF) was added slowly to an ice-cooled slurry of LiAlH$_4$ (1.3 eq, 5.2 eq hydride) in THF (1.5–2 mL/mmol ketoacid) under a N$_2$-atmosphere. The reaction mixture was stirred for 24 h at RT and then cooled with ice. Water (1 mL/g LiAlH$_4$) was added, followed by aqueous NaOH (15% w/w, 1 mL/g LiAlH$_4$)and H$_2$O (3 mL/g LiAlH$_4$). CH$_2$Cl$_2$ (2–3 mL/mmol ketoacid) and MgSO$_4$ (5–6 spoons) was added. The slurry was filtrated with a glass filter funnel and the precitate was washed with CH$_2$Cl$_2$ (3 times). The filtrate was evaporated to give the diol 6.

1-Phenyl-butane-1,4-diol (6a)

3-Benzoylpropionic acid 11a dissolved in THF was reacted with LiAlH$_4$ according to the general procedure. The following workup procedure was used: H$_2$O was added and THF was evaporated. Diethylether and HCl (2M) was added. The aqueous layer was extracted with diethylether and the combined organic layers were washed with H$_2$O, aqueous NaHCO$_3$ (saturated) and H$_2$O. Drying (MgSO$_4$), filtration and evaporation gave 80% yield of 6a. $^1$H-NMR: 7.35–7.22 (m, 5H, Ar—H); 4.70 (t, 1H, CH—OH); 3.64 (t, 2H, CH$_2$OH); 3.10 (brs, 1H, CH—OH); 2.60 (brs, 1H, CH$_2$—OH); 1.84 (q, 2H, CH$_2$—CHOH); 1.72–1.61 (m, 2H, CH$_2$CH$_2$OH).

1-(4-Methylphenyl)-butane-1,4-diol (6b)

The acid 11b was reduced according to the general procedure. Recrystallization in petroleumether/EtOAc afforded 6b 70% yield. $^1$H-NMR: 7.29–7.10 (m, 4H, Ar—H); 4.61 (t, 1H, J=6.1 Hz, Ar—CH—OH); 3.63–3.55 (m, 2H, ArCH—CH$_2$); 3.52 (brs, 2H, OH); 2.32 (s, 3H, Ar—CH$_3$); 1.77 (t, 2H, J=6.5 Hz, CH$_6$CH$_2$OH); 1.64–1.56 (m, 2H, CH$_2$CH$_2$CH$_2$OH). $^{13}$C-NMR: 141.67; 136.98; 129.00 (2C); 125.71 (2C); 74.06; 62.62; 36.15; 29.12; 21.03.

1-(4-Methoxyphenyl)-butane-1,4-diol (6c)

The acid 11c was reduced according to the general procedure and yellowish crystals of 6c were obtained in 63% yield. $^1$H-NMR: 7.28–7.24 (m, 2H, Ar—H); 6.89–6.84 (m, 2H, Ar—H); 4.65 (t, 1H, J=6.2 Hz, Ar—CH—OH); 3.79 (s, 3H, ArOC$\underline{H}_3$); 3.67–3.62 (m, 2H, C$\underline{H}_2$); 2.90 (brs, OH); 2.60 (brs, OH); 1.91–1.80 (m, 2H, C$\underline{H}_2$); 1.75–1.60 (m, 2H, C$\underline{H}_2$).

1-(4-iso-Propylphenyl)-butane-1,4-diol (6d)

The acid 11d was reduced according to the general procedure and 6d was obtained in 84% yield as a colorless oil. 1H-NMR: 7.21 (q, 4H, Ar—H.); 4.64 (t, 1H, Ar—C$\underline{H}$—OH); 3.60 (m, 2H, C$\underline{H}_2$—OH); 3.3 (brs, 1H, OH); 3.1 (brs, 1H, OH); 2.90 (sept., 1H, C$\underline{H}$—(CH$_3$)$_2$); 1.81 (q, 2H, CH—C$\underline{H}_2$); 1.63 (m, 2H, C$\underline{H}_2$CH$_2$OH); 1.23 (d, 6H, C$\underline{H}_3$).

1-(4-tert-Butylphenyl)-butane-1,4-diol (6e)

The acid 11e was reduced according to the general procedure and 6e was obtained in 92% yield white crystals. $^1$H-NMR: 7.32 (dd, 4H, Ar—$\underline{H}$); 4.70 (t, 1H, Ar—C$\underline{H}$—OH); 3.68 (t, 2H, C$\underline{H}_2$—OH); 2.6 (brs, 1H, OH); 2.2 (brs, 1H, OH); 1.85 (q, 2H, CHC$\underline{H}_2$); 1.67 (m, 2H) C$\underline{H}_2$CH$_2$OH); 1.31 (s, 9H, C$\underline{H}_3$).

1-(2,4-Dimethylphenyl)-butane-1,4-diol (6f)

The acid 11f was reduced according to the general procedure and 6f was obtained in 94% yield. $^1$H-NMR: 7.34 (d, 1H, Ar—$\underline{H}$); 7.02 (d, 1H, Ar—$\underline{H}$); 6.94 (s, 1H, Ar—$\underline{H}$); 4.90 (dd, 1H, C$\underline{H}$); 3.75–3.55 (m, 2H, C$\underline{H}_2$OH); 2.8 (brs, 2H, OH); 2.29 (s, 3H, C$\underline{H}_3$); 2.28 (s, 3H, C$\underline{H}_3$); 1.86–1.60 (m, 4H, CHC$\underline{H}_2$C$\underline{H}_2$).

1-(2-Methyl-4-methoxyphenyl)-butane-1,4-diol (6g)

The acid 11g was reduced according to the general procedure and 6g was obtained in 86% yield as yellowish crystals. $^1$H-NMR: 7.37 (d, 1H, J=8.5 Hz, Ar—$\underline{H}$); 6.76 (dd, 1H, J=8.5 and 2.5 Hz, Ar—$\underline{H}$); 6.68 (d, 1H, J=2.5 Hz, Ar—$\underline{H}$); 4.91 (t, 1H, Ar—C$\underline{H}$(OH)); 3.79 (s, 3H, OC$\underline{H}_3$); 3.55–3.45 (m, 2H, C$\underline{H}_2$—OH); 2.32 (s, 3H, C$\underline{H}_3$); 1.85–1.65 (m, 4H, C$\underline{H}_2$C$\underline{H}_2$). $^{13}$C-NMR 126.42; 115.93; 111.33; 70.47; 62.96; 55.18; 35.14; 29.56; 19.24.

1-(2,4-Dimethoxyphenyl)-butane-1,4-diol (6 h)

The acid 11 h was reduced according to the general procedure and white crystals of 6 h were obtained in 85% yield. $^1$H-NMR: 7.23 (d, 1H, J=9 Hz, Ar—$\underline{H}$); 6.51–6.46 (m, 2H, Ar—$\underline{H}$); 4.88 (t, 1H, J=6 Hz, Ar—C$\underline{H}_2$—OH); 3.83 (s, 3H, OC$\underline{H}_3$); 3.81 (s, 3H, OC$\underline{H}_3$); 3.70 (t, 2H, J=5.7 Hz, C$\underline{H}_2$—C$\underline{H}_2$—OH); 1.93–1.80 (m, 2H, C$\underline{H}_2$—CH$_2$—OH); 1.78–1.63 (m, 2H, Ar—CH(OH)—C$\underline{H}_2$). $^{13}$C-NMR: 159.69; 157.10; 127.06; 125.02; 103.91; 98.28; 69.24; 62.50; 55.12; 55.06; 34.15; 29.23.

1-(2,4,6-Trimethylphenyl)-butane-1,4-diol (6i)

The acid 11i was reduced according to the general procedure. The crude 6i was obtained in 85% yield. Recrystallization in EtOAc/petroleumether (40/60) gave 6i in 52% yield as white crystals. $^1$H-NMR: 6.80 (s, 2H, Ar—$\underline{H}$); 5.11 (dd, 1H, C$\underline{H}$); 3.66 (q, 2H, C$\underline{H}_2$OH); 2.7 (brs, 2H, OH); 2.2–1.6 (m, 4H, CHC$\underline{H}_2$C$\underline{H}_2$).

1-(2,6-Dimethyl-4-methoxyphenyl)-butane-1,4-diol (6j)

The acid 11j was reduced according to the general procedure and white crystals of 6j were obtained in 77% yield. $^1$H-NMR: 6.59 (s,2H, Ar—$\underline{H}$); 4.87–4.78 (m, 1H, Ar—C$\underline{H}$—OH); 3.84 (s, 3H, OC$\underline{H}_3$); 3.62 (t, 2H, J=5.7 Hz, C$\underline{H}_2$—OH); 2.27 (s, 3H, C$\underline{H}_3$); 2.24 (s, 3H, C$\underline{H}_3$); 2.00–1.60 (m, 4H, C$\underline{H}_2$C$\underline{H}_2$). $^{13}$C-NMR: 157.36; 137.45; 135.68; 126.92; 124.29; 110; 71.04; 67.86; 62.68; 55.25; 34.10; 30.05; 25.52; 21.23; 21; 19.69.

1-(4-Methoxyphenyl)-pentane-1,4-diol (6k)

The acid 11k was reduced according to the general procedure and a yellow oil of 6k was obtained in 91% yield. $^1$ $^{H-NMR}$: 7.25 (d, 2H, Ar—$\underline{H}$); 6.67 (d, 2H, Ar—$\underline{H}$); 4.6 (t, 1H, Ar—C$\underline{H}$—OH); 3.80 (s, 3H, C$\underline{H}_3$); 3.61 (t, 2H, C$\underline{H}_2$—OH); 2.1 (brs, 1H, OH); 1.9–1.2 (m, 7H, C$\underline{H}_2$OH).

General procedure for diols (12)

R$^{2(1)}$Li (1.1–1.2 eq) was added to a solution of phtalid (1 eq) in THF (1–2 mL/mmol phtalid). The reaction mixture was stirred for 0.5–1 h at −78° C. and under N$_2$-atmosphere followed by addition of R$^{2(2)}$MgX (2.4 eq) or LiAlH$_4$ to the dry ice-cooled reaction mixture. The cooling bath was removed and the reaction mixture was stirred for indicated time at ambient temperature followed by addition of aqueous NH$_4$Cl (saturated). The aqueous layer was extracted with CH$_2$Cl$_2$ and the combined organic layers were washed with H$_2$O, dried (MgSO$_4$) and concentrated to give the diol 12.

α-Phenyl-benzene dimethanol (12B)

Phtalid was reacted with PhLi (1 eq, 2M in cyklohexane/diethylether 75/25) according to the general procedure. The reaction mixture was then transferred to a slurry of LiAlH$_4$ in THF kept at 0° C. and under N$_2$-atmosphere. The temperature was raised to RT and the reaction mixture was stirred for 1.5 hour. H2O was added very slowly at 0° C., followed by NaOH (15%) and H$_2$O. CH$_2$Cl$_2$ and MgSO$_4$ was added. The mixture was filtrated with a glass filter funnel and the filtrate was evaporated to give 74% of 12B. $^1$H-NMR: 7.65–7.15 (m, 9H, Ar—$\underline{H}$); 5.99 (s, 1H, C$\underline{H}$(Ph)—OH); 4.63 (s, 1H, OH); 4.63 (s, 1H, OH); 4.59 (d, 1H, J=12 Hz, C$\underline{H}_2$—OH); 4.42 (d, 1H, J=12 Hz, C$\underline{H}_2$—OH);

α-iso-Propylbenzene dimethanol (12C)

Isopropylmagnesiumchlorid (2.4 eg, 2M in diethylether) was added to a solution of phtalid (1 eg) in THF according to the general procedure. The reaction mixture was stirred for at ambient temperature for 5 h . Workup gave a mixture of α-isopropyl benzene dimethanol (12C) (74%) and α,α-diisopropyl benzene dimethanol (26%). The products were separated by flash chromatography (petroleumether/EtOAc 3/2). 12C was obtained in 61% yield. $^1$H-NMR: 7.45–7.2 (m, 4H, Ar—$\underline{H}$); 4.69 (s, 2H, C$\underline{H}_2$—OH); 4.5 (d, 1H, J=8 Hz, HO—C$\underline{H}$—CH(CH$_3$)$_2$); 2.8 (brs, 2H, OH); 2.2–2 (m, 1H, C$\underline{H}$(CH$_3$)$_2$); 1.11 (d, 3H, J=7 Hz, C$\underline{H}_3$); 0.76 (d, 3H, J=7 Hz, C$\underline{H}_3$). $^{13}$C-NMR: 141.81; 137.65; 129.02; 127.73; 127.26; 127.13; 76.60; 62.39; 33.98; 19.34; 18.94.

α-Dimethylbenzene dimethanol (12D)

MeMgCl (2.4 eq, 2M in diethylether) was added to solution of phtalid (1 eq) in THF according to the general procedure. After stirring for 3 h at RT and workup. 12D was isolated in 95% yield. $^1$H-NMR: 7.25–7.15 (m, 4H, Ar—$\underline{H}$); 4.84 (s, 2H, C$\underline{H}_2$—OH); 1.69 (s, 6H, C$\underline{H}_3$).$^{13}$C-NMR: 145.33; 137.85; 131.66; 127.78; 127.02; 126.15; 74.35; 65.09; 32.20 (2C). IR: 3270; 3083; 3068; 2988; 2974; 2963; 2945; 2880; 1484; 1452; 1437; 1380; 1363; 1214; 1163; 1115; 1056; 1031; 1031; 937; 873; 763; 722.

α-Methyl-α-phenylbenzene dimethanol (12E)

Phtalid was reacted with McLi (1.1 eq, 1.6M in diethylether) for 1 h and then with PhMgCl (2M in THF) according to the general procedure. Sirring for 1.5 h at ambient temperature and workup gave acrude product in 80% yield which was purified by bulb-to-bulb destillation affording 12E in 74% yield. $^1$H-NMR: 7.7–7.2 (m, 9H, Ar—H); 4.48 (t, 1H, J=5 Hz, OH); 4.31 (dd, 1H. J=13 and 5 Hz, CH$_2$—OH); 4.12 (dd, 1H, J=13 and 5 Hz, CH$_2$—OH); 2.86 (s, 1H, OH); 1.84 (s, 3H, CH$_3$). $^{13}$C-NMR: 150.51; 146.62; 141.00; 131.20; 128.26 (2C); 127.96; 127.57; 126.95; 126.71; 125.56; 76.84; 63.71; 33.06.

α,α-Diphenylbenzene dimethanol (12F)

PhMgCl (2.5 eq, 2M in THF) was reacted with phtalid according to the general procedure. Stirring for 3 h at ambient temperature and workup gave 2F in 94% yield. $^1$H-NMR: 7.6–7 (m, 13H, Ar—H); 6.66 (d, 1H, J=7 Hz, Ar—H); 4.28 (s, 2H, CH$_2$—OH). $^{13}$C-NMR (CDCl$_3$/DMSO): 146.69; 146.53; 139.30; 131.87; 129.75; 127.56; 127.44; 127.39; 126.61; 126.60; 82.37; 64.24. IR: 3430; 3255; 3058; 3034; 2966; 2894; 1597; 1488; 1447; 1424; 1269; 1201; 1180; 1161; 1099; 1080; 1056; 1031; 1011; 1002; 955; 931; 898; 765; 702; 640; 610.

α-Methyl-α-vinylbenzene dimethanol (12G)

Phtalid was reacted with MeLi (1.6M in diethylether) for 1 hour and then with vinylmagnesiumbromid (1M in THF) according to the general procedure. Stirring for 3.5 h at ambient temperature and workup gave a crude product in 95% yield. Purification by bulb-to-bulb destillation afforded 12G in 80% yield. $^1$H-NMR: 7.45–7.20 (m, 4H, Ar—H); 6.16 (dd, 1H, J=11 and 17 Hz, CH=CH$_2$); 5.26 (d, 1H, J=17 Hz, trans in CH$_2$=CH); 5.14 (d, 1H, J=11 Hz, cis in CH$_2$=CH); 4.93 (d, 1H, J=12 Hz, Ar—CH$_2$OH); 4.59 (d, 1H, J=12 Hz, Ar—CH$_2$—OH); 1.74 (s, 3H, CH$_3$). $^{13}$C-NMR: 144.98; 143.83; 138.67; 131.85; 127.83; 127.62; 126.62; 112.14; 76.06; 64.54; 29.65.

α-Phenyl-α-vinylbenzene dimethanol (12I)

Phtalid was reacted with PhLi for 2.5 h and then with vinylmagnesiumbromid according to the general procedure. Stirring for 3 h at ambient temperature, workup, followed by bulb-to-bulb destillation gave 12I in 75% yield. $^1$H-NMR: 7.6–7.2 (m, 9H, Ar—H); 6.32 (dd, 1H, J=11 and 17 Hz, CH=CH$_2$); 5.3 (d, 1H, J=11 Hz, CH=CH$_2$); 5.14 (d, 1H, J=17 Hz, CH=CH$_2$); 4.3 (AB, 2H, J=12 Hz, CH$_2$—OH). $^{13}$C-NMR: 145.38, 144.40; 143.77; 138.84; 132.02; 128.57; 127.98; 127.82; 127.72; 127.51; 127.07; 126.96; 126.85; 126.20; 114.05; 80.37; 64.25.

We claim:

1. A process for the production of a 5–7 membered ring cyclic sulfonium salt compound comprising reacting a 1,4-, 1,5-, or 1,6-diol compound or a 5–7 membered ring cyclic ether compound with a mercapto compound and a strong protonic acid.

2. Process according to claim 1, wherein the strong protonic acid is added to the mercapto compound and the resulting mixture is added to the diol or cyclic ether compound, or the strong protonic acid is added to a mixture containing the mercapto compound and the diol or cyclic ether compound, in substantially equimolar amounts with respect to the functional groups involved.

3. Process according to claim 1, wherein the mercapto compound is a monofunctional mercaptan.

4. Process according to claim 1, wherein the mercapto compound is a di- or polyfunctional mercaptan.

5. A process according to claim 3 or 4, wherein the mercapto compound is selected from i) a monofunctional mercaptan which is methyl mercaptan; a primary, secondary, or tertiary alkyl or cycloalkyl mercaptan; an aryl mercaptan, said aryl mercaptan being unsubstituted or mono- or independently polysubstituted by alkyl, cycloalkyl, alkoxy, thioalkoxy, phenyl, phenoxy, or thiophenoxy; an arylalkyl mercaptan, said arylalkyl mercaptan being unsubstituted or mono- or independently polysubstituted by alkyl, alkoxy, or thioalkoxy; or ii) a di- or polyfunctional mercaptan of the general formula HS—[A—SH]$_m$, wherein m≧1, and A independently represents alkylene, alkylenebisaryl, or aralkylene.

6. Process according to claim 1, wherein the diol or cyclic ether compound is a monofunctional diol or cyclic ether compound.

7. Process according to claim 1, wherein the diol or cyclic ether compound is a di- or polyfunctional diol or cyclic ether compound.

8. A process according to claim 6 or 7, wherein the diol compound is selected from j) a monofunctional diol which is a 1,4-, 1,5-, or 1,6-diol, which is i) unsubstituted; or ii) mono- or independently polysubstituted by alkyl, cycloalkyl, 1-alkenyl, aryl, said aryl being unsubstituted or mono- or independently polysubstituted by alkyl, cycloalkyl, alkoxy, thioalkoxy, halogen, cyano, alkyl sulfonyl, aryl sulfonyl, aryl, aryloxy, or thioaryloxy; and/or iii) aryl fused, said aryl fused being unsubstituted or mono- or independently polysubstituted by alkyl, cycloalkyl, alkoxy, thioalkoxy, halogen, phenyl, phenoxy, or thiophenoxy; or iv) cycloalkyl fused, which is unsubstituted or mono- or independently polysubstituted by alkyl or cycloalkyl; or jj) a di- or polyfunctional diol of the general formula C—[B—C]$_w$, wherein w≧1, C independently represents a 1,4-, 1,5-, or 1,6-diol as defined above, and B independently represents alkylene, arylene, alkylenebisaryl or aralkylene.

9. A process according to claim 6 or 7, wherein the 5, 6, or 7 membered ring cyclic ether compound is selected from j) a monofunctional 5–7 membered ring cyclic ether selected from the group consisting of tetrahydrofuran, tetrahydropyran, or hexahydrooxepin, which cyclic ether is i) unsubstituted; or ii) mono- or independently polysubstituted by alkyl; cycloalkyl; vinyl; aryl, said aryl being unsubstituted or mono- or independently polysubstituted by alkyl, cycloalkyl, alkoxy, thioalkoxy, halogen, cyano, alkyl sulfonyl, aryl sulfonyl, aryl, aryloxy, or thioaryloxy; and/or iii) aryl fused, said aryl fused being unsubstituted or mono- or independently polysubstituted by alkyl, cycloalkyl, alkoxy, thioalkoxy, halogen, phenyl, phenoxy, or thiophenoxy; or iv) cycloalkyl fused, which is unsubstituted or mono- or independently polysubstituted by alkyl or cycloalkyl; or jj) a di- or polyfunctional cyclic ether of the general formula C—[B—C]$_w$, wherein w≧1, C independently represents a tetrahydrofuran, a tetrahydropyran, or a hexahydrooxepin as defined above, and B independently represents alkylene, arylene, alkylenebisaryl, or aralkylene.

10. Process according to claim 1, wherein the strong protonic acid is selected from hydrohalogenic, perhalogenic, tetrahaloboric, hexahaloantimonic, hexahaloarsenic, hexahalophosphoric, sulfonic, halogen-substituted alkyl or aryl sulfonic, phosphoric or sulfuric acid.

11. Process according to claim 10, wherein the strong protonic acid is selected from such acids which produce a 5–7 membered ring cyclic sulfonium salt compound having a non-nucleophilic anion.

12. Process according to claim 11, wherein the strong protonic acid is selected from perchloric, tetrafluoroboric, hexafluoroantimonic, hexafluoroarsenic, hexafluorophosphoric, p-toluensulfonic or triflic acid.

13. A process according to claim 1, comprising reacting (a) a mercapto compound having the formula $R^1$—SH, wherein $R^1$, in a monofunctional mercaptan, represents methyl; primary, secondary, or tertiary alkyl or cycloalkyl; aryl, said aryl being unsubstituted or mono- or independently polysubstituted by alkyl, cycloalkyl, alkoxy, thioalkoxy, phenyl, phenoxy or thiophenoxy; arylalkyl, said arylalkyl being unsubstituted or mono- or independently polysubstituted by alkyl, alkoxy or thioalkoxy; or $R^1$, in a di- or a polyfunctional mercaptan, represents —[A—SH]$_m$, wherein $m \geq 1$, and A independently represents alkylene, arylene, alkylenebisaryl, or aralkylene with (b) a diol compound selected from the group consisting of formula I:

$$I = \begin{array}{c} R^4 \; R^4 \\ R^3 \diagdown \diagup (R^5)_n \\ \phantom{R^3}\diagup(C)_n \diagdown \\ R^3 \diagup \phantom{XXX} \diagdown (R^6)_n \\ \phantom{R^3}\diagdown \diagup \\ R^2 \; R^2 \; OH \; OH \end{array}$$

wherein n is 1, 2, or 3, $R^2$ independently represents hydrogen, alkyl, cycloalkyl, or aryl;

$R^3$ independently represents hydrogen, alkyl, cycloalkyl, aryl, said aryl being unsubstituted or mono- or independently polysubstituted by alkyl, cycloalkyl, alkoxy, thioalkoxy, halogen, phenoxy or thiophenoxy;

$R^4$ independently represents hydrogen, alkyl, cycloalkyl, aryl, said aryl being unsubstituted or mono- or independently polysubstituted by alkyl, cycloalkyl, alkoxy, thioalkoxy, halogen, phenoxy or thiophenoxy; or $R^3$ and $R^4$ together form an aryl group fused with the corresponding carbon atoms of the carbon-carbon backbone chain;

$R^5$ independently represents hydrogen, alkyl, cycloalkyl, aryl, said aryl being unsubstituted or mono- or independently polysubstituted by alkyl, cycloalkyl, alkoxy, thioalkoxy, halogen, phenoxy or thiophenoxy;

$R^6$ independently represents hydrogen, alkyl, cyclkoalkyl, aryl, said aryl being unsubstituted or mono- or independently polysubstituted by alkyl, cycloalkyl, alkoxy, thioalkoxy, halogen, phenoxy or thiophenoxy; or (c) a cyclic ether compound selected from the group consisting of formula II:

$$II = \begin{array}{c} R^4 \; R^4 \\ R^3 \diagdown \diagup (R^5)_n \\ \phantom{R^3}\diagup(C)_n \diagdown \\ R^3 \diagup \phantom{XXX} \diagdown (R^6)_n \\ \phantom{R^3}\diagdown \diagup \\ R^2 \; R^2 \; O \end{array}$$

wherein n, $R^2$, $R^3$, $R^4$, $R^5$, and $R^6$ are as defined above; and (d) a strong protonic acid having the formula HX, wherein X represents a halogen or a group of the formula $MY_r$, wherein M represents Sb, P, B, As, or Cl; Y represents a halogen or oxygen; and r is an integer between 4 and 6, or X represents a group $RSO_3$ wherein R is OH, alkyl, aryl or halogen substituted aryl group, yielding a monofunctional cyclic sulfonium salt compound, when $R^1 \neq$—[A—SH]$_m$, having the following structural formula III-1:

$$\text{III-1} = \begin{array}{c} R^4 \; R^4 \\ R^3 \diagdown \diagup (R^5)_n \\ \phantom{R^3}\diagup(C)_n \diagdown \\ R^3 \diagup \phantom{XXX} \diagdown (R^6)_n \\ \phantom{R^3}\diagdown \diagup \\ R^2 \; R^2 \; \phantom{X} S^+ X^- \\ \phantom{R^2 \; R^2 \; XX} R^1 \end{array}$$

wherein n, $R^1$, $R^2$, $R^3$, $R^4$, $R^5$, $R^6$, and X are as defined above with the exception of that $R^1 \neq$—[A—SH]$_m$; or a di- or polyfunctional cyclic sulfonium salt compound, when $R^1$=—[A—SH]$_m$, having the following structural formula III-2:

$$\text{III-2} = \left\{ \begin{array}{c} R^4 \; R^4 \; (R^5)_n \\ \diagup \diagup \\ R^3 \diagdown \quad (C)_n\text{—}(R^6)_n \\ \phantom{X} \diagup \\ R^3 \diagup \phantom{X} S^+\text{——A——}S^+ \cdots \\ \phantom{X} \diagdown X^- \quad X^- \\ R^2 \; R^2 \end{array} \right\}_m$$

wherein n, m, A, $R^2$, $R^3$, $R^4$, $R^5$, $R^6$, and X are as defined above.

14. Process according to claim 13, wherein $R^1$ and n are as defined in claim 13, one of $R^2$=H and the other is aryl as defined in claim 13, $R^3$=H, $R^4$=H, $R^5$=H, $R^6$=H, and X represents $SbF_6$, $PF_6$, $BF_4$, $ClO_4$, or $CF_3SO_3$.

15. Process according to claim 13, wherein in the diol compound of I) or the cyclic ether compound of II), when n=1 and $R^3$ and $R^4$ together form a fused aryl group as defined, one $R^2$ can additionally define an 1-alkenyl, $(R^9)_2C=C(R^{10})$—, wherein $R^9$ and $R_{10}$ independently represent hydrogen, alkyl, cycloalkyl, aryl, or a 5–7 membered ring formed by $R^9$ and $R^{10}$; yielding a cyclic sulfonium salt compound having the following structural formula IV:

$$IV = (R^8)_z \begin{array}{c} R^5 \; R^6 \; R^1 \\ \diagdown \diagup \\ \phantom{X} S^+ X^- \\ \phantom{X} \diagdown R^9 \\ \phantom{XX} \diagup R^9 \\ \phantom{X} \diagup \\ R^2 \phantom{XXX} R^{10} \end{array}$$

wherein $R^1$, $R^2$, $R^5$, $R^6$, $R^8$, and X are as defined in claim 10, except that $R^1 \neq$—[A—SH]$_m$.

16. A process according to claim 5, wherein the monofunctional mercaptan is selected from the group consisting of: phenyl mercaptan, which is unsubstituted or mono- or independently polysubstituted by alkyl, cycloalkyl, alkoxy, thioalkoxy, phenyl, phenoxy, or thiophenoxy, naphthylmercaptan and benzylmercaptan, which is unsubstituted or mono- or independently polysubstituted by alkyl, alkoxy, or thioalkoxy.

17. A process according to claim 5, wherein the di- or polyfunctional mercaptan is a compound of the formula HS—[A—SH]$_m$ wherein m is as defined above and A independently is selected from the group consisting of: $C_2$–$C_{20}$alkylene, phenylene, biphenylene, naphthylene, methylenebiphenyl and xylylene.

18. A process according to claim 8, wherein the diol is selected from: j) a monofunctional diol that is ii) mono- or independently polysubstituted by vinyl, phenyl, which is unsubstituted or mono- or independently polysubstituted by alkyl, cycloalkyl, alkoxy, thioalkoxy, halogen, cyano, alkyl sulfonyl, phenyl sulfonyl, phenyl, phenoxy or thiophenoxy; and/or iii) benzo fused which is unsubstituted or mono- or independently polysubstituted by alkyl, cycloalkyl, alkoxy, halogen, phenyl, phenoxy or thiophenoxy; or jj) a di- or polyfunctional diol of the formula C—[B—C]$_w$, wherein w and C are as defined above, and B independently is selected from the group consisting of: $C_2$–$C_{20}$ alkylene, phenylene, biphenylene, naphthylene, methylenebiphenyl and xylylene.

19. A process according to claim 9, wherein the 5, 6 or 7 membered ring cyclic ether compound is selected from: j) a tetrahydrofuran, a tetrahydropyran, or a hexahydrooxepin, which is ii) mono- or independently polysubstituted by alkyl, cycloalkyl, vinyl, phenyl, which is unsubstituted or mono- or independently polysubstituted by alkyl, cycloalkyl, alkoxy, thioalkoxy, halogen, cyano, alkyl sulfonyl, phenyl sulfonyl, phenyl, phenoxy or thiophenoxy; and/or iii) benzo fused which is unsubstituted or mono- or independently polysubstituted by alkyl, cycloalkyl, alkoxy, halogen, phenyl, phenoxy or thiophenoxy; or jj) a di- or polyfunctional diol of the formula C—[B—C]$_w$, wherein w and C are as defined above, and B independently is selected from the group consisting of: $C_2$–$C_{20}$ alkylene, phenylene, biphenylene, naphthylene, methylenebiphenyl and xylylene.

20. A process according to claim 13, wherein $R^1$ in a monofunctional mercaptan is selected from the group consisting of phenyl, which is unsubstituted or mono- or independently polysubstituted by alkyl, cycloalkyl, alkoxy, thioalkoxy, phenyl, phenoxy or thiophenoxy; naphthyl and benzyl which is unsubstituted or mono- or independently polysubstituted by alkyl, alkoxy or thioalkoxy; or $R^1$ in a di- or polyfunctional mercaptan represents —[A—SHS]$_m$, wherein m is as defined above and A independently is selected from the group consisting of: $C_2$–$C_{20}$ alkylene, phenylene, biphenylene, naphthylene, methylenebiphenyl and xylylene.

21. A process according to claim 13, wherein in the diol compound of formula I:

$R^2$ independently represents hydrogen, alkyl, cycloalkyl, or

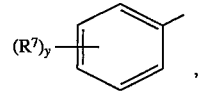

wherein y is an integer between 0 and 5, $R^7$ independently represents alkyl, alkoxy, thioalkoxy, halogen, cyano, alkyl sulfonyl, phenyl sulfonyl and phenyl, phenoxy or thiophenoxy, each of which are unsubstituted or mono- or independently polysubstituted by alkyl, cycloalkyl, alkoxy, thioalkoxy, halogen, phenoxy, thiophenoxy, cyano, alkyl sulfonyl, or phenyl sulfonyl;

$R^3$ independently represents hydrogen, alkyl, cycloalkyl, phenyl, which is unsubstituted or mono- or independently polysubstituted by alkyl, cycloalkyl, alkoxy, thioalkoxy, halogen, phenoxy or thiophenoxy;

$R^4$ independently represents hydrogen, alkyl, cycloalkyl, phenyl, which is unsubstituted or mono- or independently polysubstituted by alkyl, cycloalkyl, alkoxy, thioalkoxy, halogen, phenoxy or thiophenoxy; or $R^3$ and $R^4$ together form

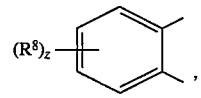

wherein z is an integer of between 0 and 4, and $R^8$ independently represent alkyl, alkoxy, thioalkoxy, halogen or phenyl, $R^5$ independently represents hydrogen, alkyl, cycloalkyl, or phenyl, which is unsubstituted or mono- or independently polysubstituted by alkyl, cycloalkyl, alkoxy, thioalkoxy, halogen, phenoxy or thiophenoxy, and $R^6$ independently represents hydrogen, alkyl, cycloalkyl, or phenyl, which is unsubstituted or mono- or independently polysubstituted by alkyl, cycloalkyl, alkoxy, thioalkoxy, halogen, phenoxy or thiophenoxy.

22. A process according to claim 15, wherein $R^9$ and $R^{10}$ independently represent hydrogen, alkyl, cycloalkyl, phenyl, or a 5–7 membered ring formed by $R^9$ and $R^{10}$.

23. A process according to claim 15, wherein $R^2$ is a vinyl group.

* * * * *